US012618078B2

(12) United States Patent
Kuzminov et al.

(10) Patent No.: US 12,618,078 B2
(45) Date of Patent: May 5, 2026

(54) CHLOROPHYTE ALGAE HAVING IMPROVED PRODUCTIVITY

(71) Applicant: PHYKION INC., La Jolla, CA (US)

(72) Inventors: Fedor Kuzminov, La Jolla, CA (US); Mahva Naghipor, La Jolla, CA (US); Moena Aqui, La Jolla, CA (US); Yingjun Wang, La Jolla, CA (US); John H. Verruto, La Jolla, CA (US)

(73) Assignee: PHYKION INC., La Jolla, CA (US)

( * ) Notice: Subject to any disclaimer, the term of this patent is extended or adjusted under 35 U.S.C. 154(b) by 1006 days.

(21) Appl. No.: 17/727,588

(22) Filed: Apr. 22, 2022

(65) Prior Publication Data

US 2022/0348946 A1     Nov. 3, 2022

Related U.S. Application Data

(60) Provisional application No. 63/179,044, filed on Apr. 23, 2021.

(51) Int. Cl.
| | |
|---|---|
| *C12N 15/82* | (2006.01) |
| *C07K 14/405* | (2006.01) |
| *C12N 1/12* | (2006.01) |
| *C12P 7/64* | (2022.01) |

(52) U.S. Cl.
CPC ........ *C12N 15/8269* (2013.01); *C07K 14/405* (2013.01); *C12N 1/12* (2013.01); *C12P 7/64* (2013.01)

(58) Field of Classification Search
CPC ........ C12N 15/8269; C12N 1/12; C12N 9/22; C07K 14/405; C12P 7/64; C12P 7/6463; C12R 2001/89
See application file for complete search history.

(56) References Cited

U.S. PATENT DOCUMENTS

| | | |
|---|---|---|
| 2014/0331357 A1 | 11/2014 | Coffin |
| 2018/0186845 A1 | 7/2018 | Zlotkin |
| 2019/0203221 A1 | 7/2019 | Ajjawi et al. |
| 2020/0157558 A1 | 5/2020 | DiPetrillo et al. |

OTHER PUBLICATIONS

Kirst H et al. Truncated Photosystem Chlorophyll Antenna Size in the Green Microalga Chlamydomonas reinhardtii upon deletion of the TLA3-CpSRP43 Gene. 2012. Plant Physiology. 2251-2260. (Year: 2012).*

Kirst et al., "The chloroplast signal recognition particle (CpSRP) pathway as a tool to minimize chlorophyll antenna size and maximize photosynthetic productivity", Biotechnol Adv, Sep. 4, 2013, 32:66-72.

PCT International Search Report and Written Opinion in International Application No. PCT/US2022/025997, dated Jul. 20, 2022, 11 pages.

* cited by examiner

*Primary Examiner* — Paul J Holland

(74) *Attorney, Agent, or Firm* — Goodwin Procter LLP

(57)     ABSTRACT

The invention involves mutant or recombinant Chlorophyte algal organisms that have a genetic modification in a gene encoding a chloroplastic signal recognition particle 43 (cpSRP43). In one embodiment the Chlorophyte organisms are Trebouxiophyte algae that are diploid or polyploid for a gene encoding a chloroplastic signal recognition particle 43 (cpSRP43). The mutant organisms can have a genetic modification in one allele of the gene but not in another allele of the gene. The mutant or algal organisms have higher biomass and lipid productivity. Additional mutant or algal organisms are disclosed that also have a genetic modification to one or more genes encoding a light harvesting chlorophyll a/b (binding) protein.

26 Claims, No Drawings

Specification includes a Sequence Listing.

CHLOROPHYTE ALGAE HAVING IMPROVED PRODUCTIVITY

CROSS-REFERENCE TO RELATED APPLICATIONS

This application claims benefit of priority under 35 U.S.C. § 119(e) of U.S. Ser. No. 63/179,044, filed Apr. 23, 2021, the entire contents of which is incorporated herein by reference in its entirety.

INCORPORATION OF SEQUENCE LISTING

The material in the accompanying sequence listing is hereby incorporated by reference into this application. The accompanying sequence listing text file name, SGI2300-1_SL.txt, was created May 3, 2022, and is 41.9 kb. The file can be accessed using Microsoft Word on a computer that uses Windows OS.

FIELD OF THE INVENTION

The invention concerns Chlorophyte algae having a genetic modification to a gene encoding a chloroplastic signal recognition particle 43 (cpSRP43), and optionally a genetic modification to a gene encoding a light harvesting chlorophyll a/b (binding) protein (LHCP) and having higher biomass and/or lipid productivity.

BACKGROUND OF THE INVENTION

Algae represent a potentially enormous resource for producing an inexpensive source of energy while limiting $CO_2$ emissions. Green algae utilize photosynthesis to harvest light energy from the sun and convert it into biomass derived from carbon dioxide and water. One limitation that limits biomass production in algae is the thermodynamic efficiency of photosynthesis in full sunlight. It is reported that up to 75% of the energy captured from the sun is wasted as heat or fluorescence.

Various methods have been applied to increase metabolic or thermodynamic efficiency and therefore increase the biomass production of algae, namely by applying methods of light dilution, rapid mixing, or improvement in the design of photobioreactors. Other methods have involved genetic approaches to increasing efficiency by engineering algal strains with reduced chlorophyll or with a reduced cross-section of the light harvesting antenna complex.

When genetic approaches are taken the use of polyploid organisms presents special challenges because such organisms can have multiple copies of relevant genes, and examples of polyploidy can be found in most major groups of algae. Therefore, the scope of algae of interest can be expanded with better genetic approaches for working with these organisms. There is therefore a continuing need for increases in photosynthetic efficiency in useful algae, including polyploid algae, in order to achieve more economically viable uses of algal products.

SUMMARY OF THE INVENTION

The invention involves mutant photosynthetic algal cells or organisms that have a genetic modification in a gene encoding a chloroplastic signal recognition particle 43 (cpSRP43). In one embodiment the organisms are Chlorophyte algae that are diploid or polyploid for a gene encoding a chloroplastic signal recognition particle 43 (cpSRP43).

The mutant organisms can have a genetic modification in one allele of the gene but not in another allele of the gene. The result is a photosynthetic algal organism with higher biomass and lipid productivity. The mutant algal organisms also optionally contain a genetic modification to one or more genes encoding a light harvesting chlorophyll a/b (binding) protein (LHCP).

In a first aspect the invention provides a mutant or recombinant Chlorophyte algal organism having a deletion, disruption, or inactivation in a first allele of a gene encoding a chloroplastic signal recognition particle 43 (cpSRP43) protein, and further having a second, active allele of the gene encoding a chloroplastic signal recognition particle 43 (cpSRP43) protein that does not comprise a deletion, disruption, or inactivation. The mutant algal organism can have at least 5% greater biomass productivity than a corresponding control organism not having the deletion, disruption, or inactivation of the first allele of the gene encoding a chloroplastic SRP43 protein. The mutant algal organism of the invention can be diploid or polyploid.

In various embodiments the mutant or recombinant Chlorophyte organism is a Trebouxiophyte algal organism, which can be of the genus *Picochlorum*. In some embodiments the mutant algal organism can have a PSII σ450 value of less than 300 A2, and a PSII σ520 value of less than 100 A2. In some embodiments the mutant algal organism can have a PSI σ450 value of less than 500 A2, and a PSI σ520 value of less than 150 A2.

In various embodiments the mutant algal organism can have a biomass productivity at least 7% higher than a corresponding control organism. The mutant algal organism can have a ratio of PSI/PSII antenna cross section of less than 1.5. The mutant algal organism can have a Chl a:b ratio of greater than 6.0.

In one embodiment the mutant algal organism has 1) a PSII σ450 value of less than 300 A2, and a PSII σ520 value of less than 100 A2; 2) a PSI σ450 value of less than 500 A2, and a PSI σ520 value of less than 150 A2; 3) a PSI/PSII value of less than 0.65; and 4) a Chl a:b ratio of greater than 6.0. The mutant algal organism can have a first allele having a sequence encoding a polypeptide with at least 85% sequence identity to SEQ ID NO: 2. The second, active allele can have a sequence encoding a polypeptide having at least 85% sequence identity to SEQ ID NO: 4. In any embodiment the mutant algal organism can further have a deletion or disruption of a gene encoding a light harvesting chlorophyll a/b binding protein of PSI and having at least 85% sequence identity to any one of SEQ ID NOs: 7-15, or any combination or sub-combination of them. The mutant algal organism can also have a deletion or disruption of a gene encoding a light harvesting chlorophyll a/b binding protein of PSI and having a polypeptide sequence with at least 85% sequence identity to any one of SEQ ID NOs: 21-29.

In one embodiment the mutant algal organism can have a deletion or disruption of a gene encoding a light harvesting chlorophyll a/b binding protein LHCP-11 of PSI, and/or a gene encoding a light harvesting complex LHCP-21 of PSI. In one embodiment the mutant algal organism has a deletion or disruption of a gene encoding a light harvesting chlorophyll a/b binding protein of PSI having a polypeptide sequence with at least 85% sequence identity to SEQ ID NOs: 21 and/or SEQ ID NO: 22. In some embodiments the mutant algal organism has a deletion or disruption of a gene encoding a light harvesting chlorophyll a/b binding protein of PSI having a sequence with at least 90% sequence identity to SEQ ID NO: 7, and a deletion or disruption of a gene encoding a light harvesting complex of PSI having a sequence with at least 90% sequence identity to SEQ ID NO: 8.

In some embodiments the mutant algal organism has a lipid productivity at least 4% higher than a corresponding control algal organism. The mutant algal organism can be a member of the genus *Picochlorum*.

In another aspect the invention provides a biomass comprising a mutant or recombinant algal organism disclosed herein.

In another aspect the invention provides a composition of lipids derived from a biomass disclosed herein.

In another aspect the invention provides a method of producing a lipid composition. The method involves culturing a mutant or recombinant cell or organism disclosed herein in a culture medium to produce a biomass composition containing lipids. The method can further have a step of harvesting a lipid product from the biomass composition.

In another aspect the invention provides a method of attenuating a pigment composition in a Trebouxiophyte algal organism. The method involves performing a deletion, disruption, or inactivation in the Trebouxiophyte algal organism in a first allele of a gene encoding a chloroplastic signal recognition particle 43 (SRP43) protein; wherein the algal organism does not have a deletion, disruption, or inactivation in a second, active allele of a gene encoding a chloroplastic signal recognition particle 43 (SRP43) protein; and cultivating the algal organism to thereby attenuate the pigment in the algal organism.

In one embodiment the Trebouxiophyte algal organism is a member of the genus *Picochlorum*. The first allele of the gene can encode a chloroplastic SRP43 protein having a polypeptide sequence with at least 85% sequence identity to SEQ ID NO: 2. The second, active allele of the gene can encode a chloroplastic SRP43 protein having a polypeptide sequence with at least 85% sequence identity to SEQ ID NO: 3. The method can involve a step of generating the deletion or disruption by exposing the algal organism to uv light and/or gamma radiation. The Trebouxiophyte algal organism can further a deletion or disruption of a gene encoding a light harvesting (binding) protein having a polypeptide sequence with at least 85% sequence identity to any one of SEQ ID NO: 21-29.

DETAILED DESCRIPTION OF THE INVENTION

The invention involves mutant Chlorophyte organisms that have a genetic modification in a gene encoding a chloroplastic signal recognition particle (cpSRP). The chloroplast signal recognition particle (cpSRP) pathway is responsible for transport of nucleus encoded light harvesting pigment-protein complexes in the stroma of the plastid and their integration into the thylakoid membranes. A chloroplastic signal recognition particle of particular interest is cpSRP43, an approximately 43 kD protein encoded by the cpSRP43 gene.

The mutant or recombinant Chlorophyte algal cell or organism having a genetic modification described herein can have greater biomass productivity and a reduced pigment content compared to a corresponding (control) organism not having the genetic modification. The mutant or recombinant cells or organism can also optionally have a reduced chlorophyll content and/or a reduced PSII antenna size compared to a corresponding control cell or organism not having the genetic modification. In various embodiments the genetic modification(s) described herein can result in substantial increases in lipid productivity and/or biomass productivity.

The chloroplast signal recognition particle (cpSRP) consists of an evolutionarily conserved 54-kDa subunit (cpSRP54) and a unique 43-kDa domain (cpSRP43). cpSRP may bind light-harvesting chlorophyll a/b binding proteins (LHCPs) to form a cpSRP/LHCP transit complex, which targets the LHCPs to the thylakoid membrane. The mutant or recombinant photosynthetic algal cells or organisms of the invention can have a genetic modification to a gene encoding a cpSRP43 domain.

The recombinant cell or organism of the invention having a genetic modification described herein can have higher lipid productivity (e.g. as measured by FAME) and/or higher biomass productivity than a corresponding (control) cell or organism. In any embodiment the genetic modification can be a deletion, inactivation, disruption, or knockout of a gene encoding a chloroplastic signal recognition particle 43 (cpSRP43) domain.

Biomass productivity can be measured as the rate of biomass accumulation, for example as the total organic carbon (TOC) content of the respective cells or organisms. In one embodiment the lipid and/or biomass productivity of a mutant or recombinant algal cell or organism described herein is higher in batch culture (i.e. a culture where nutrients are not renewed or re-supplied to the medium during culturing) compared to a corresponding (control) cell or organism. Any of the cells or organisms disclosed herein can be photosynthetic algal cells or organisms. Any of the mutant or recombinant algal cells or organisms described herein can exhibit increased lipid productivity and/or increased biomass productivity under photoautotrophic conditions compared to a corresponding control cell or organism, i.e. conditions where the mutant or recombinant cells or organisms can produce their own biomass using light, carbon dioxide, water, and nutrients via photosynthesis. Corresponding (control) cells or organisms are cells or organisms that are useful for evaluating the effect of any one or more of the genetic modifications. "Corresponding (control) cells or organisms" are cells or organisms that do not have the one or more genetic modifications being evaluated and that are subjected to the same or substantially the same conditions as the test cells or organisms such that a difference in the performance or characteristics of the cells or organisms is based only on the genetic modification(s) being evaluated. In any embodiment the corresponding (control) cells or organisms can be of the same genus and/or species as the test organism. They can also be the same or similar in every way except for the one or more genetic modification (s) being evaluated. In some embodiments the corresponding (control) cell or organism is a wild-type cell or organism. But the corresponding (control) cell or organism can also be a laboratory strain or parental strain of the test cell or organism. Substantially the same conditions can be the same conditions or slightly different conditions where the difference does not materially affect the function, activity, or expression of the nucleic acid sequence modified in the cell or organism. Substantially the same conditions can mean substantially the same culturing conditions. Persons of ordinary skill know appropriate cultivation conditions for particular types of cells and applications. In any embodiment cultivation conditions can be any appropriate conditions as known to persons of ordinary skill. In other embodiments cultivation conditions can be simulated outdoor conditions with a light profile that resembles mid-spring in a desert climate. In one embodiment the conditions can be correspond to those of the Imperial Valley, California, e.g. temperatures and light conditions in a statistically typical month of May. In one embodiment the conditions can involve about 2000 μE at noon, with a constant temperature of 30° C. Cultures can be grown in urea-containing medium and can be continuously stirred with 1% CO2 supplied through a fritted sparger. However, persons of ordinary skill will readily be able to set appropriate conditions for particular studies and comparisons.

The lipid products of the mutant or recombinant photo-synthetic algal cells or organisms described herein can be further processed into biomass, biofuels, or used in the production of other specialty chemical products. In some embodiments the genes encoding the cpSRP43 protein or domain can be SEQ ID NO: 1 or 2, or a sequence having at least 80% or at least 85% or at least 90% or at least 95% or at least 98% sequence identity to any one or more of SEQ ID NO: 1 or 2; or can be a sequence that encodes a polypeptide having at least 80% or at least 85% or at least 90% or at least 95% or at least 98% sequence identity to SEQ ID NO: 3 or SEQ ID NO: 4.

In some embodiments the mutant or recombinant algal photosynthetic organisms of the invention are diploid or polyploid organisms. A cell or organism having two paired (homologous) sets of chromosomes is diploid. Polyploid organisms have more than two paired (homologous) sets of chromosomes. In various embodiments the organisms of the invention are diploid or polyploid. In any embodiment the mutant or recombinant photosynthetic algal cell or organism is a diploid or polyploid organism that is heterozygous for a genetic modification at the cpSRP43 gene, meaning that it has more than one allele (or copy) of the cpSRP43 gene and that at least one allele (or copy) has the genetic modification (e.g. a deletion, disruption, or inactivation) and another copy does not. In one embodiment the organism is diploid and has two alleles (or copies) of the cpSRP43 gene, and one allele has a genetic modification (e.g. a deletion, disruption, or inactivation), and the other does not, i.e. the organism is heterozygous for a mutation at the cpSRP43 gene. In other embodiments the organism is homozygous for a genetic modification at the cpSRP43 gene and all alleles of the cpSRP43 gene have the genetic modification. In one embodiment the organism is diploid and homozygous for the genetic modification at the cpSRP43 gene and both alleles of the cpSRP43 gene have the genetic modification.

In any embodiment the mutant or recombinant cells or organisms of the invention can have a reduced amount of chlorophyll b, and can have an increased chlorophyll a to chlorophyll b ratio (chl a/chl b) compared to a corresponding control cell or organism, which can be at least 20%, at least 30%, at least 40%, at least 50%, at least 60%, at least 70%, at least 85%, at least 100%, or at least 150%, or at least 200% higher than the chl a/chl b ratio of a corresponding (control) cell or organism. The mutant or recombinant cells or organisms of the invention can have a chl a/chl b ratio of at least 4.0 or at least 5.0 or at least 6.0 or at least 7.0 or at least 8.0 or at least 9.0 or at least 10.0. In any embodiment the mutant or recombinant cells or organisms of the invention can have a p, connectivity value of less than 0.50, or less than 0.45, or less than 0.40, or less than 0.35, or less than 0.30. In various embodiments the mutant or recombinant cells or organisms of the invention can have a PSI/PSII ratio of less than 0.75, or less than 0.70, or less than 0.65, or less than 0.60, or a PSI/PSII ratio at least 15% or at least 20% or at least 25% lower than that of the corresponding control cell or organism. In various embodiments the mutant or recombinant cells or organisms of the invention can have a PSII σ450 value of less than 300 A², or less than 250 A², or less than 225 A², or less than 200 A², and can have a PSII σ520 value of less than 125 A², or less than 100 A², or less than 75 A², or less than 60 A². Any of the mutant or recombinant cells or organisms of the invention can have any one, any two, or more than two of the values described above. In any embodiment the mutant or recombinant cells or organisms of the invention can have a TOC productivity of greater than 17.0 g/m2/day or greater than 17.5 or greater than 18.0 or greater than 18.5 or greater than 19.0 g/m2/day, or at least 10% higher or at least 12% higher or at least 14% higher, or at least 15% higher than a corresponding control cell or organism.

In various embodiments the mutant or recombinant cells or organisms of the invention can have a PSII σ450 value of less than 300 A² and a PSII σ520 value of less than 125 A², a PSI σ450 of less than 500 A², and a PSI σ520 of less than 150 A². In another embodiment the mutant or recombinant cells or organisms of the invention can have a PSII σ450 value of less than 250 A² and a PSII σ520 value of less than 100 A², a PSI σ450 of less than 400 A², and a PSI σ520 of less than 125 A². In another embodiment the mutant or recombinant cells or organisms of the invention can have a PSII σ450 value of less than 225 A² and a PSII σ520 value of less than 75 A², a PSI σ450 of less than 350 A², and a PSI σ520 of less than 100 A². Optionally, any of the mutant or recombinant cells or organisms of the above embodiments can further have 1) an Fv/Fm of greater than 0.60; or 2) an a(chl)(m2/g TOC) of less than 0.38 or less than 0.35 or less than 0.30; or 3) an Nchl/PSII of less than 250 or less than 150 or less than 100 and/or an Nchl/PSI of less than 300 or less than 225 or less than 150; or 4) a PSII/TOC (e.g. by fluorescence induction and relaxation (FIRe)) of less than 18.0 or less than 15.0 or less than 13.0.

The recombinant cells or organisms can have decreased photosynthetic antenna size, for example a reduced photo-system II (PSII) and/or a reduced photosystem I (PSI) antenna size. In various embodiments the cross-sectional unit size of the PSII and/or PSI antenna of the recombinant cells or organisms disclosed herein can be reduced by at least 5%, or at least 10%, at least 20%, at least 30%, at least 25%, at least 30%, at least 35%, at least 40%, at least 45%, at least 50%, or at least 60% compared to the PSII and/or PSI antenna size of a corresponding (control) cell or organism. σ520 and σ450 values of PSI and PSII can be used as a measure of respective antenna sizes.

The mutant or recombinant cells or organisms can have a higher growth rate and/or a higher biomass productivity than a corresponding control cell or organism not having the genetic modification, for example, in either case higher by at least 5% or at least 10% or at least 15% or at least 20%, or at least 25%. The mutant or recombinant cells or organisms can have higher biomass productivity per hour or per day or per period of 2 days or 3 days or 4 days or 5 days or 6 days, for example, at least 5% higher, or at least 10%, or at least 15%, or at least 20%, or at least 25% higher than a corresponding control cell or organism. "Biomass" refers to cellular mass, whether of living or dead cells. Biomass productivity, or biomass accumulation, or growth rate, can be measured by any means accepted in the art, for example as ash free dry weight (AFDW), dry weight, wet weight, or total organic carbon (TOC) productivity. In any embodiment biomass productivity, or biomass accumulation, or the growth rate, can be measured as total organic carbon (TOC) productivity.

The mutant or recombinant cells or organisms of the invention can produce a greater amount of a bioproduct per time period (e.g. per minute or per hour or per day or per period of 2 days or 3 days or 4 days or 5 days or 6 days), for example a lipid product or total lipids (e.g. measured as FAME) than a corresponding (control) organism. The amount of product can be expressed as g/time period, mg/time period, ug/time period, or any other defined quantity per defined time period described herein. Such bioproducts can be isolated from a lysate or biomass or cellular secretion of any of the mutant or recombinant cells or organisms of the invention. In some embodiments, the mutant or recombinant cells or organisms of the invention produce at least 5%, or at least 10%, at least 15%, at least 20%, at least 25%, at least 30%, at least 35%, at least 40%, at least 45%, at least 50%, at least 60%, at least 70%, at least 80%, at least 90% or at least 100% more of the bioproduct than a corresponding control cell or organism cultured under the substantially the same conditions, i.e. have higher lipid productivity. In various embodiments any of the parameters described herein can be measured under batch culturing conditions, semi-continuous culturing conditions, or continuous culture conditions. In various embodiments the conditions can be nutrient replete culture conditions or nitrogen deplete conditions. In any embodiment the conditions can be photoautotrophic conditions.

Without wanting to be bound by any particular theory it is believed that the genetic modifications described herein result in an attenuation or elimination of expression of at least one cpSRP43 protein domain. Such attenuation or elimination results in a significant increase in lipid and/or biomass productivity in the cell. Lipid productivity in one embodiment can be measured as the total FAME produced by the cell; biomass productivity can be measured by the organic carbon produced by the cell (as measured, for example, by total organic carbon).

A "recombinant" or "engineered" nucleic acid molecule or sequence is a nucleic acid molecule or sequence that has been altered through human manipulation. As non-limiting examples, a recombinant nucleic acid molecule or sequence includes any nucleic acid molecule or sequence that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in Nature; 3) has been engineered using molecular biology techniques such that it lacks one or more nucleotides with respect to the naturally occurring nucleic acid molecule sequence, or that it has been engineered to cause a disruption, inactivation, insertion, or deletion in a gene sequence; and/or 4) has been manipulated using molecular biology techniques such that it has one or more sequence changes or rearrangements with respect to the naturally occurring nucleic acid sequence, or has a sequence (e.g. by insertion) not found in the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

A mutant or recombinant cell or organism of the invention is one that has been manipulated to have a genetic modification described herein (e.g. a deletion, attenuation, inactivation, or disruption or "knock out" in one or more alleles of one or more gene(s)). In some embodiments the genetic modification can be to one or more alleles of a gene encoding an cpSRP43 protein or domain, and/or to one or more alleles of a gene encoding a light harvesting chlorophyll a/b (binding) protein (LHCP). As used herein, a mutant or recombinant organism or cell includes progeny or derivatives of the mutant or recombinant cells or organisms of the disclosure.

Any of the mutant or recombinant algal cells or organisms described herein can be generated by human intervention, for example, by classical mutagenesis, genetic engineering (e.g. by CRISPR/Cas9), insertion/deletion mutations, homologous recombination, or by any method. Screening methods can be used to identify mutants having desirable characteristics e.g., reduced chlorophyll and/or carotenoids or other pigments, and increased lipid and/or biomass productivity.

Algal Cell or Organism

The mutant or recombinant algal cell or organism of the invention can be a microalga, or a photosynthetic organism, or a green alga. The mutant or recombinant alga can be any eukaryotic microalga such as, but not limited to, a Chlorophyte, an Ochrophyte, or a Charophyte alga. In some embodiments the mutant or recombinant microalga can be a Chlorophyte alga of the taxonomic Class Chlorophyceace, or of the Class Chlorodendrophyceae, or the Class Prasinophyceace, or the Class Trebouxiophyceae, or the Class Eustigmatophyceae. In some embodiments, the mutant or recombinant microalga can be a member of the Class Chlorophyceace, such as a species of any one or more of the genera *Asteromonas, Ankistrodesmus, Carteria, Chlamydomonas, Chlorococcum, Chlorogonium, Chrysosphaera, Dunaliella, Haematococcus, Monoraphidium, Neochloris, Oedogonium, Pelagomonas, Pleurococcus, Pyrobotrys, Scenedesmus,* or *Volvox.* In other embodiments the mutant or recombinant microalga of the invention can be a member of the Order Chlorodendrales, or Chlorellales. In other embodiments, the mutant or recombinant microalga can be a member of the Class Chlorodendrophyceae, such as a species of any one or more of the genera *Prasinocladus, Scherffeha,* or *Tetraselmis.* In further alternative embodiments, the mutant or recombinant alga can be a member of the Class Prasinophyceace, optionally a species of any one or more of the genera *Ostreococcus* or *Micromonas.* Further alternatively, the mutant microalga can be a member of the Class Trebouxiophyceae, and optionally of the Order Chlorellales, and optionally a genera selected from any one or more of *Botryococcus, Chlorella, Auxenochlorella, Heveochlorella, Marinichlorella, Oocystis, Parachlorella, Pseudochlorella, Tetrachlorella, Eremosphaera, Franceia, Micractinium, Nannochloris, Picochlorum, Prototheca, Stichococcus,* or *Viridiella,* or any of all possible combinations or sub-combination of the genera. In another embodiment the recombinant alga can be a Chlorophyte alga of the Class Trebouxiophyceae and the Order Chlorellales and the genus *Picochlorum.* Or of the family Chlamydomonadaceae and the genus *Chlamydomonas* (e.g. *Chlamydomonas reinhardtii*); or of the family Volvocaceae and the genus *Volvox* (e.g. *Volvox carteri, Volvox aureus, Volvox globator*). Or of the Class Trebouxiophyceae and the family Coccomyxaceae, and the genus *Coccomyxa* (e.g. *Coccomyxa subellipsoidea*).

In another embodiment the mutant or recombinant alga is a Chlorophyte alga of the Class Trebouxiophyceae, or Eustigmatophyceae, and can be of the Order Chlorellales or Chlorodendrales, and can be of the Family Oocystaceae, or Chlorellaceae, or Monodopsidaceae, and optionally from a genus selected from one or more of *Oocystis, Parachlorella,*

*Picochlorum, Nannochloropsis,* and *Tetraselmis.* The recombinant alga can also be from the genus *Oocystis,* or the genus *Parachlorella,* or the genus *Picochlorum,* or the genus *Tetraselmis,* or from any of all possible combinations and sub-combinations of the genera. In one embodiment the recombinant algal cell or organism is of the Class Trebouxiophyceae, of the Order Chlorellales, and optionally of the family Oocystaceae, and optionally can be of the genus *Oocystis.*

An "allele" is one of two or more versions of a gene. In any embodiment two or more alleles of a gene can have a very high degree of sequence identity to each other, for example at least 90%, or at least 95% or at least 96%, or at least 97% or at least 98%, or at least 99%, or at least 99.5% or 100% sequence identity between any two alleles of a gene, and the same levels of sequence identity can be present between proteins encoded by any two alleles of a gene. In any embodiment the sequence identity can be calculated considering only the coding sequence of a gene. Different alleles of a gene can encode the same protein, which can have nucleotide sequences having at least 90%, or at least 95% or at least 96%, or at least 97% or at least 98%, or at least 99%, or at least 99.5% sequence identity to each other, but encode proteins having the same function. Alleles of a gene can encode proteins having little or no observable change in the function of the proteins encoded by different alleles of a gene. The encoded genes can have the same or identical function. But different alleles of a gene can provide different observable phenotypic traits (e.g. different pigment composition or pigmentation level of a cell or organism). Mutant or recombinant cells or organisms of the invention can be heterozygous for a genetic modification or mutation at different alleles of a gene or be homozygous for a mutation at different alleles of a gene. The state of being heterozygous or homozygous at alleles of the cpSRP43 gene can result in differences in phenotypic traits, e.g. observable pigmentation composition or pigmentation levels of the cells or organisms having the different alleles. Different phenotypes can be detected using any method described herein (e.g. flow cytometry, any photophysiological parameter, or any combination or sub-combination of them, as disclosed herein).

In a particular embodiment of the invention the mutant recombinant alga of the invention is a diploid organism and has two copies of the gene encoding a cpSRP43 domain. In one embodiment the organism has an allele A and an allele B of the gene encoding the cpSRP43 domain, and either allele A or allele B (or both) have a genetic modification described herein. In one embodiment the genetic modification can be a deletion, disruption, or inactivation at either allele A or allele B, and in one embodiment the deletion, disruption, or inactivation is at allele A, and allele B is unmodified. But in another embodiment the deletion, disruption, or inactivation is at allele B, and allele A is unmodified. In one embodiment the recombinant organism is of the Order Chlorellales, and can be of the genus *Picochlorum.*

In various embodiments the mutant or recombinant algal cell or organism of the invention has a deletion, disruption, or inactivation in a first allele of a gene encoding a chloroplastic signal recognition particle 43 (cpSRP43) protein, and has a second, active allele of the gene encoding a chloroplastic signal recognition particle 43 (cpSRP43) protein that does not comprise a deletion, disruption, or inactivation. The second "active" allele is an allele that functions normally, the same or essentially the same as in a corresponding (control) cell or organism.

In some embodiments the mutant recombinant algal organism of the invention is heterozygous at alleles of the cpSRP43 gene. In some embodiments the mutant algal organism has a genetic modification at allele A of the cpSRP43 gene, and the mutant algal organism does not have a genetic modification at allele B of the cpSRP43 gene. In some embodiments allele A comprises SEQ ID NO: 1 or a variant thereof, and allele B comprises SEQ ID NO: 3 or a variant thereof. In various embodiments the genetic modification can be to a nucleic acid sequence having at least 75%, or at least 80%, or at least 85%, or at least 90%, or at least 95% or at least 98% sequence identity to SEQ ID NO: 1 (allele A) or SEQ ID NO: 3 (allele B). The cpSRP43 gene at allele A can encode SEQ ID NO: 2, or a variant thereof, and the cpSRP43 gene at allele B can encode SEQ ID NO: 4, or a variant thereof.

The genetic modification can be to a nucleic acid sequence encoding a polypeptide having at least 75%, or at least 80%, or at least 85%, or at least 90%, or at least 95%, or at least 98% sequence identity to SEQ ID NO: 2 or 4. In one embodiment the genetic modification is to a nucleic acid sequence having at least 75%, or at least 80%, or at least 85%, or at least 90%, or at least 95%, or at least 98% sequence identity to SEQ ID NO: 1. In one embodiment the genetic modification is to a nucleic acid sequence encoding a polypeptide having at least 75%, or at least 85%, or at least 90%, or at least 95%, or at least 98% sequence identity to SEQ ID NO: 2 (encoding an allele A polypeptide); and the organism can, optionally, have an allele B of the cpSRP43 gene that is unmodified. An unmodified allele or nucleic acid sequence can be one having a wild type or laboratory strain allele or nucleic acid sequence that has not been subjected to mutagenesis or genetic engineering.

In one embodiment the genetic modification is to a nucleic acid sequence having at least 75%, or at least 80%, or at least 85% or at least 90% or at least 95% or at least 98% sequence identity to SEQ ID NO: 3 (allele B). In one embodiment the genetic modification is to a nucleic acid sequence encoding a polypeptide having at least 75%, or at least 80%, or at least 85%, or at least 90%, or at least 95%, or at least 98% sequence identity to SEQ ID NO: 4 (encoding an allele B polypeptide); and the organism can, optionally, have an allele A of the cpSRP43 gene that is unmodified.

Genetic Modification

In various embodiments the recombinant alga of the invention can have a genetic modification to a gene encoding a cpSRP43 domain. In some embodiments the recombinant alga is a diploid organism and has the genetic modification to allele A of the cpSRP43 gene, and optionally does not have a genetic modification to allele B of the cpSRP43 gene. In one embodiment the genetic modification is to a native or endogenous sequence of the cell or organism. An unmodified gene or nucleic acid sequence present naturally in the organism denotes a natural, endogenous, or wild type sequence.

A "genetic modification" can be any one or more of a deletion, a mutation, a disruption or knockout, an insertion, insertion of a stop codon, an inactivation, an attenuation, a rearrangement, one or more point mutations, a frameshift mutation, an inversion, a single nucleotide polymorphism (SNP), a truncation, a point mutation, or another genetic modification that changes the activity, expression, or function of the one or more genes or nucleic acids having the modification. In some embodiments the genetic modification results in an attenuation of activity, expression, or function of the gene. In any embodiment the genetic modification can be created by human intervention, i.e. the genetic modification can be as a result of deliberate steps taken by a human agent. The genetic modification can be made or be present in any sequence that affects expression or activity of the gene or nucleic acid sequence, or the nature or quantity of its product, for example to a coding or non-coding sequence, a promoter, a terminator, an exon, an intron, a 3' or 5' UTR, or other regulatory sequence of the gene or nucleic acid sequence; a genetic modification performed in any structure of the gene or nucleic acid sequence can result in a reduction, attenuation, or elimination of the gene or nucleic acid product or activity. In one embodiment the genetic modification is a deletion, disruption, or inactivation. The genetic modification can be made to or be present in the host cell's native genome. In some embodiments, a mutant or recombinant cell or organism having attenuated expression of a gene as disclosed herein can have one or more mutations, which can be one or more nucleobase changes and/or one or more nucleobase deletions and/or one or more nucleobase insertions, into the region of a gene 5' of the transcriptional start site, such as, in non-limiting examples, within about 2 kb, within about 1.5 kb, within about 1 kb, or within about 0.5 kb of the known or putative transcriptional start site, or within about 3 kb, within about 2.5 kb, within about 2 kb, within about 1.5 kb, within about 1 kb, or within about 0.5 kb of the translational start site. In diploid or polyploid organisms any type of genetic modification disclosed herein can be present in one allele of a gene but not another, or in both or all alleles of a gene. Whether a genetic modification is heterozygous or homozygous may affect the activity, expression, or function of a gene. In one embodiment it may change the phenotype of an organism carrying the genetic modification(s).

An "attenuation" is a genetic modification resulting in a reduction of the function, activity, or expression of a gene or nucleic acid sequence compared to a corresponding (control) cell or organism not having the genetic modification being examined, i.e. the diminished function, activity, or expression is due to the genetic modification. The activity of a nucleic acid sequence can be expression of an encoded product, a binding activity (e.g. RNA binding), or other activity the nucleic acid sequence exerts within the organism. In various embodiments an attenuated gene or nucleic acid sequence produces less than 90%, or less than 80%, or less than 70%, or less than 50%, or less than 30%, or less than 20%, or less than 10%, or less than 5% or less than 1% of its function, activity, product, or expression of the gene or nucleic acid sequence compared to the corresponding (control) cell or organism. In various embodiments a gene attenuation can be achieved via a deletion, a partial deletion, a disruption, or an inactivation. Any of the genetic modifications described herein can result in partial or complete attenuation of the function, activity, or expression of the attenuated gene or nucleic acid sequence.

A "deletion" is a genetic modification in which at least part of the target nucleic acid sequence is deleted. Deletion can cause a loss of expression, activity, or function of a gene or nucleic acid sequence—which loss can be complete or partial. Deletions can be directed to the coding or non-coding sequence or regulatory sequence of a gene, and in some embodiments can be present at one allele of a gene but not another. A deletion can be a complete deletion, in which all function, activity, or expression of the gene or nucleic acid sequence is eliminated. A deletion with respect to a gene can thus involve the loss of only a part of the nucleotide sequence of the gene, which can still result in a complete loss of expression, activity, or function of the gene or nucleic acid sequence. When the organism is polyploid a homozygous deletion is a deletion at all copies of the gene. Deletion of a small number of base pairs, or a small number of base pairs in a multiple of three (e.g. 3 bp or 6 bp) that does not change the expression, activity, or function (e.g. conferred phenotype) of the gene is not considered a deletion.

A "disruption" (or "knock out") involves the insertion or deletion of a nucleotide sequence into or from the coding, non-coding, or regulatory portion of a gene with resulting complete loss of product, activity, or expression of the gene or allele, i.e. the product, activity, or expression of the gene (or allele) is completely knocked out or disrupted. A disruption (or other genetic modification) at one allele of a gene can affect the phenotype, activity, or expression of the gene. Disruptions or knock outs can be accomplished in various ways, for example by the insertion or deletion of a sequence into or from any sequence or regulatory sequence of a gene (e.g. a selection marker), a combination of deletion and insertion, or the insertion of a stop or nonsense codon, the generation of a frameshift mutation in a gene or part thereof, or the use of double-stranded breaks generated by programmable nucleases, or by various other means of inserting or deleting nucleotide sequences in the sequence of a gene. In non-limiting examples a disruption or knock out can be accomplished using CRISPR-Cas9, homologous recombination, site-specific nucleases, zinc-finger nucleases, or transcription activator-like effector nucleases (TALENS).

An "inactivation" is a genetic modification causing loss of product, activity, or expression of the inactivated gene or nucleic acid sequence. An inactivation can be reversible or irreversible (for example the reversible or irreversible binding of a component to one or more parts of the gene or nucleic acid sequence). An inactivation can be partial or complete, and result in the partial or complete loss of product, activity, or expression of the inactivated gene (or allele of a gene).

Functional expression refers to the expression of a functional product or activity of a nucleic acid sequence. When the expressed product of a nucleic acid is a polypeptide, functional expression means expression of polypeptide activity having at least 10% or at least 25% or at least 50% or at least 75% of the activity of the polypeptide product in an unmodified cell or organism. For activity of a gene or nucleic acid sequence functional expression means expression or activity of at least 10% or at least 25% or at least 50% or at least 75% of the expression or activity of the gene or nucleic acid sequence in a corresponding (control) cell or organism not having the modification and cultivated under the same or substantially the same conditions.

Thus, various types of genetic modifications can be given terms that overlap in description. Persons of ordinary skill know that the particular term describing a genetic modification can be dependent both on how a gene or its components, or a nucleic acid sequence, is being physically changed as well as on the context. The mutant or recombinant cells or organisms of the invention can have any of the types of genetic modifications described herein.

In one embodiment the genetic modification is a deletion or disruption involving the introduction of a stop codon into at least one allele of a cpSRP43 gene (including regulatory sequences) or nucleic acid sequence, as described herein. For example, the genetic modification can be a stop mutation or nonsense mutation introduced into SEQ ID NOs: 1 or 3, or into a variant of either, or into a nucleic acid sequence encoding the polypeptide of SEQ ID NO: 2 or 4 or a variant of either polypeptide sequence. In one embodiment the genetic modification is a modification that results in a stop mutation (or nonsense mutation) being inserted into at least a first allele (e.g. allele A) of a gene coding for a cpSRP43 gene and, optionally, a second allele of the cpSRP43 gene does not contain a deletion, disruption, or inactivation (e.g. allele B).

"Variant" sequences are sequences having at least 60% sequence identity or at least 70% sequence identity, or at least 75%, or at least 80%, or at least 85%, or at least 90%, or at least 95%, or at least 98% sequence identity to another sequence to the reference sequence, e.g. a nucleotide, ribonucleotide, or polypeptide sequence of any of SEQ ID NOs: 1-29.

The genetic modification can also be a stop mutation or nonsense mutation introduced into at least one allele of a gene or nucleic acid sequence encoding a cpSRP43 gene or nucleic acid sequence disclosed herein. In various embodiments the gene or nucleic acid sequence is SEQ ID NO: 1 or 3 or a variant sequence thereof, or a gene or nucleic acid sequence encoding the polypeptide of SEQ ID NO: 2 or 4, or a polypeptide variant sequence thereof, which mutation can be introduced at any location of the sequence or into a regulatory sequence governing the sequence. Modification can result in a termination of transcription from the gene prior to its natural point of termination. Thus, in one embodiment the mutation is the introduction of a stop codon that functionally deletes or disrupts the activity or expression of at least one allele of the gene or nucleic acid sequence. The stop codon or other modification can also be introduced at any of various different loci or locations within at least one allele of a gene encoding a cpSRP43 domain, or in a regulatory sequence, for example at a promoter, terminator, or other regulatory sequence that attenuates the gene or the activity of the encoded polypeptide, and that results in deletion, disruption, or inactivation (or functional deletion) of the gene. Analogous modifications can be made to the sequence(s) for similar effect. Such insertion or deletion or other mutation can also cause a loss of product, function, or activity of the at least one allele of a gene encoding a cpSRP43 domain, and result in the effect of increased biomass productivity and/or increased lipid productivity as disclosed herein.

Any of the recombinant cells or organisms of the invention can have a reduced functional absorption cross section of PSII and/or reduced PSII antenna size compared to a corresponding (control) cell or organism that does not have a genetic modification described herein and cultivated under the same or similar conditions. For example, the cross-sectional unit size of the PSII antenna can be reduced by at least 10%, at least 20%, at least 30%, at least 25%, at least 30%, at least 35%, at least 40%, at least 45%, at least 50%, at least 60%, at least 70%, or at least 80% compared to the functional absorption cross section of PSII and/or PSII antenna size of the corresponding (control) cell or organism not having the genetic modification. In some embodiments the recombinant cells or organisms of the invention can additionally (and optionally) have a reduced functional absorption cross section of PSI or reduced PSI antenna size by the same amounts stated above versus a corresponding (control) cell or organism.

In some embodiments, a mutant or recombinant photosynthetic cell or organism disclosed herein can have an increased Fv/Fm ratio compared to a corresponding control cell or organism. For example, the mutant or recombinant photosynthetic cell or organism can have Fv/Fm that is at least 5%, at least 10%, at least 12%, at least 15%, at least 20%, at least 30%, at least 40% or at least 50% higher than that of a corresponding (control) photosynthetic cell or organism. In various embodiments the Fv/Fm can be 5-50%, or 5-30% or 5-20% higher than that of corresponding control photosynthetic cell or organism.

Further, a mutant or recombinant photosynthetic cell or organism as provided herein can have an increased rate of electron transport on the acceptor side of photosystem II compared to a corresponding (control) organism. The rate can be at least about 20%, 30%, 40%, 50%, 60%, 80%, or 100% higher compared to the corresponding control cell or organism. In addition, mutant or recombinant photosynthetic cells or organisms of the invention can have a rate of carbon fixation (Pmax (C)) that is higher than a corresponding control organism. For example, Pmax (14C) can be at least about 20%, 30%, 40%, 50%, 60%, 80%, or 100% higher than that of a corresponding control cell or organism.

In some embodiments, the mutant or recombinant cells or organisms of the invention have decreased PSI and/or PSII antenna size and can optionally also have a higher amount of a ribulose bisphosphate carboxylase activase (Rubisco activase or "RA") than a corresponding (control) organism. For example, the amount of RA can be at least 1.2, 1.4, 1.6, 1.8, 2, 2.2, or 2.5 fold higher than the amount of RA in a corresponding control cell or organism. In some embodiments, the mutants demonstrate reduced expression of at least one, or at least two, or at least three, or at least four, or at least five, or six, or eight, or ten, or twelve, or fourteen LHCP genes and increased expression of an RA gene. Thus, the mutant or recombinant cells or organisms of the invention can be mutant or recombinant photosynthetic cells or organisms having reduced chlorophyll and reduced PSII antenna size, where the mutants have a higher amount of Rubisco activase than corresponding control photosynthetic cells or organisms.

The ratio of PSI to PSII antenna sizes can be important for robustness in a cell or organism, and any introduced imbalance between the size of the PSII antenna relative to PSI can lead to a loss in efficiency of photosynthesis. Any of the mutant or recombinant cells or organisms of the invention can have a ratio of PSI/PSII antenna cross section of less than 1.6 or less than 1.5 or less than 1.4 or less than 1.3 or between 1.15-1.40 or 1.20-1.40 or 1.20-1.35 or 1.20-1.30. This can be present in combination with the higher biomass productivities and other desirable cell attributes disclosed herein for the mutant or recombinant cells or organisms. Thus, a mutant or recombinant cell or organism of the invention can have a ratio of PSI/PSII antenna cross section disclosed herein, and also have a biomass productivity at least 5% or at least 7% or at least 9% greater than a corresponding control cell or organism. In one embodiment PSI/PSII can be measured using a Joliot type (JTS-10) LED pump-probe spectrometer, or equivalent.

Light Harvesting Complex (LHC)

The light harvesting complex (LHC) is an array of protein and chlorophyll, and other pigment molecules embedded in the thylakoid membrane and provide the antenna system of the photosynthetic apparatus. LHCs can be composed of several light harvesting chlorophyll a/b (binding) proteins (LHCPs), which are integral membrane proteins. They are associated with photosystems I and II (PSI and PSII) and normally exist in a pigment-protein complex containing chlorophyll a, chlorophyll b, and xanthophylls.

In some embodiments a recombinant algal mutant of the invention can have a genetic modification in one or more genes encoding an LHCP, which modification can be a deletion, disruption, or inactivation. The genetic modification can be in addition to a genetic modification of one or more alleles of cpSRP43 gene(s) described herein. In some embodiments one, two, or more than two LHCP genes can be deleted, disrupted, or inactivated in the mutant or recombinant algal cells or organisms disclosed herein. The LHCP genes can be LHCP-PSI genes, LHCP-PSII genes, or a combination of LHCP-PSI and LHCP-PSII genes. In various embodiments the modified genes can be any one or more of SEQ ID NO: 7-15, or a variant of any. In some embodiments one or two or three LHCP-PSI genes are modified, which optionally, can be selected from any one or more of SEQ ID NOs: 7-15, or variants of any of them, disclosed as if set forth fully herein in all possible combinations and sub-combinations. In some embodiments the LHCP-PSI genes can have the sequence of SEQ ID NO: 7 or SEQ ID NO: 8, or a variant of either. In various embodiments the mutant or recombinant algae can have a genetic modification to SEQ ID NO: 7 and/or SEQ ID NO: 8, or variants of either or both. In some embodiments the LHCP-PSI gene can be LHCP-11, or can be LHCP-21, or can be both LHCP-11 and LHCP-21. In any embodiment the mutant algal organism can be of the genus *Picochlorum*. In various embodiments the LHCP genes having the genetic modification can encode a polypeptide having at least 60% sequence identity or at least 70% sequence identity or at least 75% or at least 80% or at least 85% or at least 90% or at least 95% or at least 98% sequence identity to of any one or more of SEQ ID NO: 21-29, disclosed as if set forth herein in all possible combinations and sub-combinations.

Thus, in some embodiments the recombinant cells or organisms of the invention have at least 2, or at least 4, or at least 6, or at least 8, or at least 10, or at least 12 LHCP-PSI and/or LHCP-PSII genes that are deleted, disrupted, or inactivated or otherwise modified or downregulated compared to their expression level in a corresponding (control) cell or organism. In various embodiments the reduction in expression of the one or more LHCP genes can be a reduction of at least 20%, or at least 30%, or at least 40%, or at least 50%, or at least 60%, or at least 70% in the level of LHCP transcripts compared to the control cell or organism.

The structure of a gene consists of many elements, of which the protein coding sequence is only one part. The gene includes nucleic acid sequences that are not transcribed and sequences that are untranslated regions of the RNA. Genes also contain regulatory sequences, which includes promoters, terminators, enhancers, silencers, introns, 3' and 5' UTRs, and coding sequences, as well as other sequences known to be a part of genes. In various embodiments any of these structures or nucleic acid sequences can have one or more of the genetic modifications described herein that result in the higher lipid productivity and/or higher biomass productivity as described herein.

Persons of ordinary skill know how to calculate the percent of "sequence identity" between two sequences. Any method of determining sequence identity that has acceptance by most persons of ordinary skill in the art or otherwise widely accepted in the field can be utilized to determine the sequence identity between two sequences. In one embodiment the percent of sequence identity can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268). In one embodiment the search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx can be the BLOSUM62 matrix (Henikoff (1992), Proc. Natl. Acad. Sci. USA 89, 10915-10919). For blastn the scoring matrix can be set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Lipid Productivity

The recombinant mutant algae of the invention having a genetic modification to a gene or nucleic acid sequence encoding a chloroplastic SRP43 protein as described herein can demonstrate an increase in the production of lipid in the cell or organism versus a corresponding (control) cell or organism. The increase in lipid production can be measured by any accepted and suitable method, for example using fatty acid methyl ester (FAME) analysis. In one embodiment the increase in lipid production is measured as an increase in total FAME produced by the recombinant organisms. The mutant or recombinant cells or organisms of the invention having a genetic modification to a cpSRP43 gene or nucleic acid sequence can exhibit at least 5% or at least 10% or at least 15% or at least 20% or at least 30% or at least 40% or at least 50% or at least 60% or at least 70% or at least 80% or at least 90% or at least 100% greater lipid productivity compared to a corresponding control cell or organism, as described herein. In other embodiments the increase in lipid productivity can be 5-10% or 5-12% or 5-15% or 15-25% or 15-35% or 15-45% or 15-50% or 25-45% or 25-55% or 25-70% or 25-90% or 25-100% or 25-150% or 25-200% or 30-35% or 30-45% or 30-55%. In one embodiment the increase can be weight for weight (w/w). In one embodiment lipid productivity and an increase thereto is measured using the FAME profile (fatty acid methyl ester assay) of the respective cells or organisms. In one embodiment lipid productivity can be expressed as mg/L. In other embodiments the recombinant cells or organisms of the invention can exhibit at least 50 g/m2 or at least 60 or at least 70 or at least 80 grams per square meter of FAME accumulation after 5 days of cultivation. Methods of producing a FAME profile are known to persons of ordinary skill in the art. A FAME profile can be determined using any suitable and accepted method, for example a method accepted by most persons of ordinary skill in the art.

An increase in lipid productivity can be measured by weight, but can also be measured in grams per square meter per day of the surface of a cultivation vessel (e.g. a flask, photobioreactor, cultivation pond). In various embodiments the recombinant alga of the invention produce at least 3 or at least 4 or at least 5 or at least 6 or at least 7 or at least 8 or at least 10 or at least 12 or at least 13 or at least 14 grams or at least 15 or at least 20 grams per square meter per day of lipid product, which can be measured by any convenient and accepted measure, e.g. the FAME profile. In any of the embodiments the high lipid and/or high biomass productivity phenotype can be obtained under any conditions disclosed herein, e.g. under nitrogen deplete conditions, which in some embodiments can involve dilution and/or replacement of medium with fresh nitrogen deplete medium during growth. Dilutions can be by any suitable amount, for example dilution by about 50% or by about 60% or by about 70% or at least 70%, or by about 80%, or by more than 80%. In one embodiment the lipid product is a fatty acid and/or derivative of a fatty acid. In one embodiment the fatty acids and/or derivatives of fatty acid comprise one or more species of molecules having a carbon chain between C8-C18 and/or C8-C20 and/or C8-C22 and/or C8-C24, in all possible combinations and sub-combinations. In one embodiment the growth conditions can be batch growth, involving spinning cells to remove nitrogen from the medium, replacing with nitrogen deplete medium, and resuming batch growth.

In any of the embodiments the genetic modification to the gene or nucleic acid sequence encoding the cpSRP43 protein can result in an attenuation of expression of one or both of the alleles of the gene (e.g. allele A, but not allele B, or vice versa). The genetic modification of any one or more of these allele A and/or allele B of the gene encoding the cpSRP43 protein can be any of those described herein. In one embodiment the genetic modification is a deletion, disruption, or inactivation. In another embodiment the genetic modification is a deletion (which optionally, can be a functional deletion) or a disruption of the gene.

Biomass Productivity

The recombinant algal cells of the invention having a genetic modification to a gene or nucleic acid encoding a cpSRP43 protein can also have higher biomass productivity than a corresponding (control) organism not having the genetic modification. Biomass can be measured as total organic carbon (TOC), known to persons of ordinary skill in the art. The recombinant cells can have at least 5% higher or at least 10% higher or at least 12% higher or at least 15% higher or at least 20% higher or at least 25% higher or at least 30% higher or at least 35% higher, or at least 50% higher or at least 60% higher or at least 70% higher or at least 80% higher or at least 90% higher or at least 100% higher or at least 125% higher or at least 150% higher or at least 200% higher biomass productivity than a corresponding (control) cell or organism, which in one embodiment can be measured by total organic carbon (TOC) analysis. In other embodiments the biomass productivity can be 5-10% or 5-12% or 5-15% or 15-35% or 15-40% or 25-45% or 15-50% or 25-70% or 50-100% or 50-200%.

Various methods of measuring total organic carbon are known to persons of ordinary skill in the art. Biomass productivity can be measured as mg/ml of culture per time period (e.g. 1 day or 2 days or 3 days or 4 days or 5 days). In some embodiments the higher biomass productivity and/ or higher lipid productivity as described herein can occur under nitrogen deplete conditions. Thus, in one embodiment the recombinant alga of the invention can have higher lipid production and/or higher total organic carbon production than a corresponding (control) cell or organism, which higher amount can be produced under nitrogen deplete or low nitrogen conditions. Nitrogen deplete conditions can involve culturing in a buffer having less than 0.5 mM of nitrogen in any available form external to the cell or organism. In one embodiment the cells can be cultured in 0.5 mM or less of KNO3 or urea as a nitrogen source. Other buffers may also be used and be nitrogen deplete if they contain a level of nitrogen that does not change the physiology of a nitrogen-related parameter (e.g. lipid productivity or biomass productivity) by more than 10% versus culturing the cell in a medium free of a nitrogen source external to the cells or organisms. In any embodiment biomass productivity can be evaluated by measuring an increase in the total organic carbon of the cells. Nutrient replete conditions are those where the growth of the cultivated organism is not limited by a lack of any nutrient.

In various embodiments the one or more genetic modification(s) can be made in (i.e. derived from) a cell or organism that is a wild type, parent, or laboratory strain. Laboratory strains are cells or organisms that have been cultured in a laboratory setting for a period of time sufficient for the strain to undergo some adaptation(s) advantageous to growth in the laboratory environment and render the strain distinctive versus a more recently cultured wild-type strain. Laboratory strains nevertheless can be genetically modified as described herein and yield significant desirable characteristics from the genetic modification(s), as described herein. For example, laboratory strains can have higher biomass productivity and/or higher lipid productivity than a wild-type strain. In some embodiments one or more genetic modifications disclosed herein can be performed on a laboratory strain to result in a recombinant algal organism of the invention. In such embodiments the laboratory strain can therefore be a corresponding control algal cell or organism described herein that does not have the genetic modification being considered.

Methods of Producing a Lipid

The invention also provides methods for producing a lipid product. The methods involve culturing a mutant or recombinant algal cell or organism described herein to thereby produce a lipid product. Any of the methods can also involve a step of harvesting lipid produced by the recombinant algal cell or organism. The culturing can be for a suitable period of time, for example, at least 1 day or at least 3 days or at least 5 days.

The invention also provides methods for producing a composition containing lipids. The methods involve culturing a mutant or recombinant algal cell or organism described herein to thereby produce a composition containing lipids. The composition can be a biomass composition. The cultivating can be done in any suitable medium conducive to algal growth (e.g. an algal growth or culture medium or any medium described herein). The methods can also involve a step of harvesting lipids from the composition or biomass containing lipids. The methods can involve a step of harvesting lipids from the mutant or recombinant cells or organisms. Any of the methods herein can also involve a step of purifying the lipid containing composition to produce a biofuel or biofuel precursor. A biofuel precursor is a composition containing lipid molecules that can be purified into a biofuel.

The methods can involve exposing algal cells or organisms to a treatment of uv light or gamma radiation. Mutant or recombinant cells that produce high quantities of lipids can be identified by contacting the recombinant cells with a stain that identifies lipids (e.g. by BODIPY dye). Optionally, methods can include a step of isolating lipids from the mutant or recombinant algal organisms. The mutant or recombinant alga can be cultivated in any suitable growth media for algae, such as any of those described herein. The uv light or gamma radiation treatment can involve, for example, subjecting the culture to uv light, or gamma radiation, or both, for a suitable period of time or under a suitable uv regimen or gamma radiation regimen. Persons of ordinary skill understand suitable regimens for uv light or gamma radiation exposure for mutagenesis. The uv regimen can involve exposing the cells or organisms to uv light, which can be performed in batches with each batch receiving a dose. Multiple cell batches can receive different doses of energy for each batch of cells. For example 4 or 5 batches of cells can receive doses of exposure to 16-57 uJ/cm2 of energy, and exposure energy can increase with each separate batch. The cell batches can be pooled together after exposures are complete. The recombinant alga (or pooled algae) can be cultivated for at least 2 days or at least 3 days, or at least 4 days, or at least 5 days, or at least 6 days, or at least 10 days, or at least 20 days, or from 2-10 days, or from 2-20 days or from 2-25 days after exposure. The recombinant algal organisms can be any described herein.

Any of the recombinant cells or organisms of the invention can be cultivated in batch, semi-continuous, or continuous culture to produce the higher biomass productivity and/or higher lipid productivity. In various embodiments the culture medium can be nutrient replete, or nitrogen deplete (–N). In some embodiments the culturing is under photoautotrophic conditions, and under these conditions inorganic carbon (e.g., carbon dioxide or carbonate) can be the sole or substantially the sole carbon source in the culture medium.

The invention also provides a biofuel comprising a lipid product of any of the recombinant cells or organisms described herein. The biofuel is produced by purifying a lipid containing composition disclosed herein and produced by a mutant or recombinant algal cell or organism described herein.

FAME and TOC Analysis Methods

The lipid productivity of the cells or organisms can be measured by any method accepted in the art, for example as an increase or decrease in fatty acid methyl esters comprised in the cell, i.e. FAME analysis. In some embodiments any of the mutant or recombinant algal cells or organisms of the invention can have higher biomass productivity as described herein versus corresponding control cells or organisms. In some embodiments the recombinant algal cells or organisms of the invention can have higher lipid productivity and also higher biomass productivity compared to a corresponding per liter (mg/L), and for algae, may be reported as grams per square meter per day (g/m2/day). In semi-continuous assays, mg/L values are converted to g/m2/day by taking into account the area of incident irradiance (the SCPA flask rack aperture of 1½ inches×3⅜", or 0.003145 m2) and the volume of the culture (550 ml). To obtain productivity values in g/m2/day, mg/L values are multiplied by the daily dilution rate (30%) and a conversion factor of 0.175. Where lipid or subcategories thereof (for example, TAG or FAME) are referred to as a percentage, the percentage is a weight percent unless indicated otherwise. The term "fatty acid product" includes free fatty acids, mono-di, or tri-glycerides, fatty aldehydes, fatty alcohols, fatty acid esters (including, but not limited to, wax esters); and hydrocarbons, including, but not limited to, alkanes and alkenes).

Photosynthetically fixed carbon in microalgal cultures was determined by the difference between dissolved inorganic carbon in media (IC) and total carbon (TC) using a total organic carbon analyzer equipped with combustion catalytic oxidation at 720° C. and evolution of CO2 from inorganic carbonaceous species with a reactor of phosphoric acid. The evolved CO2 from both reactors was air-swept to a non-dispersive infrared (NDIR) detector where the combustion profile peak area was quantified by a linear regression calibration curve built from standard solutions of potassium hydrogen phthalate and sodium bicarbonate. Cultures were diluted with water prior to analysis to prolong combustion catalyst lifetime.

Photophysiological Parameters

A list of measured known photophysiological parameters utilized in the field of the invention is provided in Table 1, a number of which were measured in the invention. Any one or more of these parameters, and any combination or subcombination of them, can be used to assess the effect of a genetic modification on the mutant or recombinant cells or organisms disclosed herein.

TABLE 1

| Parameter | Description |
|---|---|
| $F_V/F_M$ | Quantum efficiency of PSII photochemical reactions |
| $\sigma_{450}$ (A$^2$): PSII | Functional cross-section of PSII measured with blue excitation |
| $\sigma_{520}$ (A$^2$): PSII | Functional cross-section of PSII measured with green excitation |
| $N_{Chl}$/PSII | Estimated number of chlorophyll molecules per PSII |
| PSII/TOC (FIRe) | Estimated number of photosystems II |
| p, connectivity | Measure of "energy sharing" between photosystems |
| $\sigma_{450}$ (A$^2$): PSI | Functional cross-section of PSI measured with blue excitation |
| $N_{Chl}$/PSI | Estimated number of chlorophyll molecules per PSI |
| PSI/PSII (JTS10) | Estimated ratio of PSI/PSII |
| $a_{Chl}$ (m$^2$/g TOC) | Absorption cross-section normalized to TOC |
| Chl/TOC (%) | Relative chlorophyll content |
| Chl a:b | Measured chlorophyll a to chlorophyll b ratio |
| (V-B)/V | Ratio of fluorescence upon blue/violet excitation that is proportional to chlorophyll a to chlorophyll b ratio |
| B/FSC | Ratio of fluorescence upon blue laser excitation over the forward scattering-proportional to the total chlorophyll content | control cell or organism. Biomass productivity can be measured by any methods accepted in the art, for example by measuring the total organic carbon (TOC) content of a cell. Embodiments of both methods are provided in the Examples.

"FAME lipids" or "FAME" refers to lipids having acyl moieties that can be derivatized to fatty acid methyl esters, such as, for example, monoacylglycerides, diacylglycerides, triacylglycerides, wax esters, and membrane lipids such as phospholipids, galactolipids, etc. In some embodiments lipid productivity is assessed as FAME productivity in milligrams Example 1—Generation of Mutants The amino acid sequence of cpSRP43 in *Parachlorella* sp. was analyzed against the *Picochlorum* sp. genome to identify the best gene candidate. The gene candidates identified were named C4075215 (SEQ ID NO: 1) and C4067888 (SEQ ID NO: 3). In order to generate *Picochlorum* mutants we used a Cas9 editor strain that was transformed with guide RNAs designed to target the cpSRP43 gene.

A Cas9 editor strain was generated via the heterologous expression of Cas9 using an intron-less Cas9 gene that was placed under the control of a strong promoter/terminator pair (SEQ ID NOs: 5 and 6) taken from the LHCP-PSII gene of *Picochlorum*. This construct was transformed into a *Pico-chlorum* wild-type strain and generated mutants were confirmed by PCR and sequencing. Sequence analysis was performed by aligning the reference sequence with the amplified sequences from the mutants to determine if the site was interrupted with either an insert having the selection marker cassette or some other insertion/deletion event. Primers were designed to amplify the part of the genome targeting the mutation site. Expression of Cas9 was also verified by western blot. The highest expressing clone was selected and named STR30208. The generated Cas9 editor strain was electroporated with three guide RNAs (SEQ ID NOs: 18-20) and a ZeoR selectable marker in the form of a PCR product with no HR arms so editing was mediated by non-homologous end joining (NHEJ). The generated mutants were than screened to confirm the phenotype. cpSRP43 mutants can also be generated by standard methods, e.g. through the deletion, disruption, or inactivation of the cpSRP43 gene using random mutagenesis and screening, and the photosystems using 1) the ratio of fluorescence upon blue laser excitation over the forward scattering—(B/FSC), proportional to the total chlorophyll content, and 2) the ratio of fluorescence upon blue/violet excitation (V-B)/V that is proportional to the chlorophyll a to chlorophyll b ratio.

As indicated in Table 2a-b, low light acclimated cultures of *Picochlorum* sp. homozygous cpSRP43 deletion mutants demonstrated a substantial reduction in the functional PSII antenna to about 35 N(chl)/PSII, which suggests no light harvesting chlorophyll a/b proteins (LHCPs) were attached to the core complex. The absence of antenna complexes leads to a reduction in the connectivity parameter (since a smaller antenna means that the excitation energy could not be as easily shared between neighboring photosystems) while FV/FM remained high, suggesting that in spite of losing LHCPs, the algae were in a functional state and did not show any impairment in growth. Chlorophyll b was identified only in trace amounts. The PSI antenna size appeared to be significantly smaller than in the wild type strain. It was therefore likely that a substantial loss in the LHCP-PSIs also occurred. Table 3 below presents photophysiological data for SRP43 deletion clones grown under low light/medium light conditions (300 pmol photons/m2/s).

TABLE 2a

Photophysiological parameters of *Picochlorum* wild type and cpSRP43 deletion lines grown under low light/medium light conditions (300 umol photons/m2/s). Errors shown in brackets.

| Strain ID | σ450 (A²) PSII | σ520 (A²) PSII | N(chl)/PSII | Fv/Fm | p, connectivity | a(chl) (m²/g TOC) | Chl/TOC % |
|---|---|---|---|---|---|---|---|
| STR30208 (Cas9 mother) | 524(2) | 159(1) | 308 | 0.60 (0.01) | 0.45 (0.01) | 0.34 | 8 |
| SRP43 1 | 96(1) | 25(1) | 31 | 0.62 (0.01) | 0.30 (0.01) | 0.19 | 2.8 |
| SRP43 2 | 98(1) | 26(1) | 36 | 0.62 (0.01) | 0.32(0.010 | 0.18 | 3.1 |
| SRP43 3 | 98(1) | 26(1) | 39 | 0.63 (0.01) | 0.30 (0.01) | 0.19 | 3.6 |
| SRP43 4 | 98(1) | 26(1) | 35 | 0.61 (0.01) | 0.31 (0.01) | 0.19 | 3.2 |
| SRP43 5 | 97(1) | 25(1) | 32 | 0.62 (0.01) | 0.29 (0.01) | 0.2 | 3.0 | or by employing targeted nucleases (e.g. zinc finger nucleases, TALENs, or CRISPR-associated proteins).

Example 2—Screening for Mutants

Rapid screening for the phenotype of lower pigment level was based on multiple excitation flow cytometry, particularly by calculation of (V-B/V) and (B/F S). Green algae contain two types of chlorophyll (chl a and chl b) and carotenoids. A significant portion of carotenoids and chlorophyll b are located within the light harvesting antenna, while chlorophyll a is associated with both light harvesting antenna and the photosystems. Thus, it was hypothesized that in antenna-reduced mutants chlorophyll b and carotenoid content may be lower (when normalized to chlorophyll a content), which can be indicated by lower absorption in the 450-500 nm and about 650 nm spectral regions. A flow cytometer equipped with three lasers was used to measure violet at 405 nm excitation; blue at 488 nm excitation, and yellow at 561 nm excitation. Fluorescence excitation was thus effectively probed at three distinct wavelengths. By using at least two wavelengths an estimate was made of the partitioning of pigment between the light harvesting antenna TABLE 2b Photophysiological parameters of *Picochlorum* wild type and cpSRP43 deletion lines grown under low light/medium light conditions (300 umol photons/m2/s). Errors shown in brackets.

| Strain ID | Chl | V-B/V | B/FSC |
|---|---|---|---|
| STR30208 (Cas9 mother) | 3.88 | 0.91 | 0.18 |
| SRP43 1 | >10 | 5.65 | 0.04 |
| SRP43 2 | >10 | 5.62 | 0.04 |
| SRP43 3 | >10 | 5.65 | 0.04 |
| SRP43 4 | >10 | 5.68 | 0.04 |
| SRP43 5 | >10 | 5.71 | 0.04 |

Several mutants showed mutation in either allele A or allele B of the SRP43 gene, or both, as revealed by sequencing and data in Table 3. STR30310 was a homozygous mutant having both allele A and allele B of the SRP43 gene deleted and had the most reduced pigment/antenna (Table 3). STR30309 was a heterozygous mutant that had a disruption in allele A and had an intermediate phenotype. STR30309 also had an in-frame loss of three base pairs at allele B that did not further change the phenotype. Heterozygous mutants with a deletion at allele B and a wild type (wt) at allele A had the wild type phenotype (mutants 24 and 9).

TABLE 3

Photophysiology of *Picochlorum* mutants with a heterozygous and homozygous KO in cpSRP43 genes under PSE light conditions*.

| Strain ID | (V-B)/V*10 | B/FSC | allele A | allele B |
|---|---|---|---|---|
| 12 | 0.76 | 0.2 | wt | wt |
| 24 | 0.86 | 0.19 | wt | insert |
| 9 | 0.9 | 0.18 | wt | insert |
| STR27251 | 0.92 | 0.18 | wt | wt |
| STR30309 (He) | 2.46 | 0.1 | Zeo insert | 3 bp del (in frame) |
| STR30310 (Ho) | 4.81 | 0.06 | 2 bp deletion | 2 bp deletion |

Tables 4 and 5 present data showing that a heterozygous deletion of cpSRP43 having allele A of cpSRP43 deleted but allele B present gives an intermediate or "mild" phenotype (STR30309) characterized by a substantial drop in the functional antenna sizes of PSII and PSI while maintaining relatively high connectivity and quantum efficiency of PSII. The heterozygous deletion led to a more pronounced reduction in the functional antenna size of PSII compared to PSI, and was also accompanied by a reduction in the PSII/PSI ratio. A homozygous deletion of both alleles A and B of cpSRP43 resulted in a "severe" phenotype (STR30310) having an even larger reduction in the functional cross-section of PSII (the PSI functional cross-section was observed as being more reduced compared to STR30309), while having a loss of connectivity. Strain STR30309 having the heterozygous deletion of cpSRP43 at allele A had a substantial reduction in pigment (as measured by flow cytometry and chlorophyll extractions) while maintaining relatively balanced PSI/PSII ratio and high efficiency of PSII as shown by Fv/Fm, and also exhibited improved biomass productivity.

TABLE 4

Photophysiological parameters of *Picochlorum* wild type and two cpSRP43 KO lines grown under photosynthetic efficiency (PSE) light conditions*.

| Strain ID | σ450 (A²) PSII | σ520 (A²) PSII | σ450 (A²) PSI | σ520 (A²) PSI | Fv/Fm | p, connectivity | a(chl) (m²/g TOC) |
|---|---|---|---|---|---|---|---|
| STR27251 | 460(2) | 150(1) | 626(34) | 204(11) | 0.58(0.01) | 0.48(0.01) | 0.41(0.02) |
| STR30309 SRP43 He | 198(1) | 54(1) | 332(40) | 90(11) | 0.63(0.01 | 0.40(0.01) | 0.23(0.01) |
| STR30310 SRP43 Ho | 136(1) | 35(1) | — | — | 0.61(0.01) | 0.29(0.02) | 0.21(0.01) |

TABLE 5

Photophysiological parameters of *Picochlorum* wild type and two cpSRP43 KO lines grown under photosynthetic efficiency (PSE) light conditions*.

| Strain ID | N(chl)/ PSII | N(chl) PSI | PSI/PSII (JTS10) | PSII/TOC (FIRe)** | Chl/TOC % | Chl a:b | Biomass productivity (g/m²/day) |
|---|---|---|---|---|---|---|---|
| STR27251 | 294(1) | 400(21) | 0.79(0.08) | 18.9(0.1) | 9.9)0.2) | 4.64 | 16.9 |
| STR30309 SRP43 He | 78(11) | 130(23) | 0.58(0.08) | 12.4(0.1) | 3.9(0.1) | >10 | 19.5 |
| STR30310 SRP43 Ho | 41(1) | — | — | 9.3(0.1) | 2.9(0.1) | >10 | 16.2 |

*PSE light conditions involve simulated outdoor conditions with a light profile that resembles May 4th Imperial Valley (CA, USA) day (~2000 µE noon); temperature is kept constant at 30° C., cultures are grown in urea-containing medium and are continuously stirred with 1% CO2 supplied through a fritted sparger.
**fluorescence induction and relaxation method.

The data show that the mutant or recombinant cell or organism of the invention has a biomass productivity of about 15% higher than that of the corresponding control cell or organism. The cells or organisms of the invention also have a PSI/PSII ratio of about 25% less than that of the corresponding control cells or organism, and a N(chl)PSII of more than 70% lower, and a N(chl)PSI of more than 65% lower than the corresponding control organism.

Example 3—Deletion or Disruption of LHCPs

It was found that strain STR30309, having a heterozygous deletion of cpSRP43, does not reduce the pigment of PSII and PSI in a linear manner. Instead, the created imbalance in antenna sizes was compensated for by an opposite imbalance in the PSI/PSII ratio. Therefore, attempts were made to further reduce the PSI antenna in STR30309 by deleting or disrupting genes of the light harvesting chlorophyll a/b proteins (LHCP).

Ten different genes were identified that putatively encoded LHCP-PSI in the strain (Table 6).

TABLE 6

| Gene ID | Target Status | Strains and genes deleted or disrupted |
| --- | --- | --- |
| 3377421 | RNA guide design; transformed | None |
| 3376703 | RNA guide design; transformed | STR30309 + LHCP-21 |
| 3379623 | RNA guide design; transformed | STR30309 + LHCP-11 + LHCP-21 |
| 3380741 | None | None |
| 3382021 | RNA guide design; transformed | None |
| 3382646 | None | None |
| 3380921 | RNA guide design; transformed | None |
| 3380916 | RNA guide design; transformed | None |
| 3376704 | None | None |
| 3379622 | None | None |

LHCP-PSI mutants were generated in STR30309, the SRP43 heterozygous line with cpSRP43 allele A deleted (Table 3). Six guide RNAs were designed to target six different LHCP-PSI genes: T3377421 (SEQ ID NO: 9), T3376703 (SEQ ID NO: 7) with guide RNA (gRNA) target of SEQ ID NO: 16), T3379623 (SEQ ID NO: 8) with a gRNA target sequence of SEQ ID NO: 17), T3382021 (SEQ ID NO: 10), T3380921 (SEQ ID NO: 11), T3380916 (SEQ ID NO: 12). All six guide RNAs were transformed along with a NatR selectable marker in the form of a PCR product having no HR arms; therefore editing was mediated by NHEJ. One mutant was found to have a homozygous NatR integration in the T3379623 (SEQ ID NO: 8) locus making it a double deletion or disruption (cpSRP43+LHCP-11) (STR30831). Another mutant had homozygous indels in the T3376703 (SEQ ID NO: 7) and T3379623 (SEQ ID NO: 8) loci, and thus a triple deletion or disruption (SRP43+LHCP-11+LHCP-21) (STR30843). Photophenotyping of the two mutant strains along with double SRP54/CheY KO lines under photosynthetic efficiency (PSE) conditions is presented in (Table 7).

TABLE 7

| Strain ID | σ450 (A2): PSI | σ450 (A2): PSII | Ratio of PSI/PSII antenna cross-section | Biomass productivity (g/m2/day) |
| --- | --- | --- | --- | --- |
| STR27251 (wt) | 626 (34) | 460 (2) | 1.36 | 18.2 |
| STR30208 (Cas9 mother) | 620 (15) | 447 (3) | 1.39 | 17.8 |

TABLE 7-continued

| Strain ID | σ450 (A2): PSI | σ450 (A2): PSII | Ratio of PSI/PSII antenna cross-section | Biomass productivity (g/m2/day) |
| --- | --- | --- | --- | --- |
| STR30309 (cpSRP43 He) | 332 (40) | 198 (1) | 1.68 | 19.9 |
| STR30831 (SRP43 + LHCP-11) | 237 (24) | 217 (2) | 1.09 | 19.1 |
| STR30843 (cpSRP43 + LHCP11 + LHCP-21) | 269 (24) | 216 (2) | 1.25 | 20.0 |

Analysis revealed that further specific reduction in the antenna size of PSI in the LHCP mutants occurs. PSI and PSII are more balanced and closer to the wild type in these mutants than in the parental STR30309 strain. STR30843 showed a ratio of PSI to PSII cross-section close to that of the wild-type (wt). Biomass productivity of the cpSRP43+ LHCP-11 knock out was about 5% higher than for the wt. Biomass productivity of the cpSRP43+LHCP-11+LCH-21 triple KO was about 10% higher than the wild type. However, the triple knock out also had much better balance between PSI and PSII antenna sizes, as shown by the PSI/PSII ratio being much closer to the wild type. Therefore, these cells are expected to be more robust and more useful in production.

SEQ ID NO: 1, *Picochlorum* sp., DNA, C4075215
sequence_region_id = 918410 start = 16762 stop = 15644
length = 1119, allele A of cpSRP43
ATGGAAATCATAAACAGAAATTTCATTATTGCGATTGGTCCTCATACC

AGGACCGCTCCTCGACCTGGAATCCGTAGGACAAGGCAGGTGCTGCACGACACTGG

TGCAAGACGGGCCCTGTTTGTCTTCCAGACGACTCCCCGAGCGTGCAAAGCCCAAGC

TAGGTTGATGATCCAAGCTGCGACTGAGGAAATTGTCGAGGTCAAGAATCTGAAAG

GCATTCGAATGAAACCGCGCAGCGCCGAGGACGAGGAGAAAAAGGTTCGTCCAATG

GTGGAGTACTTGGTAGAGTGGAAGGATGGGTCGCCAGATACATGGGAGCCCGTCAC

AAACCTCGCGGACAATTTGCTGAGAGATTTTGAATCCAAATGGTGGAACGCTGTCAA

AAAGGGAGACGAAGCTGTGATGAGCGAGATGCTCGACGGCGGAGGCGCTGTTTTGT

CACGAACCCTGAATGAGGACAGGCGCAGTGCTCTCCATTTTGCGGCTGCTCTTGGGA

AAGCTGACCTGGTGCGGCGTCTCATCAGAGAGGGGGCCGAGGTGGACCTGGGAGAT

-continued

AAAGAAGGGTACACTCCTCTGCACATGGCCGCAGGATATCTTCATACATCGACAATA

TACGCTTTGATAGAAGGGAATGCAGATCCAGAGCAGCAGGATTTGCAGGGCAGGTC

TCCCTTGGAACTTGTCGAAAGCCTGAGAGCAGCTCTGCCCCCGGATAATCCAGCGAC

TGCGGCTCGTAGAATTGCTCTAGAAGAGGTACTGAAAGTATTGGTGGATAATTTGTT

CGAAGATGTGCTTCCAGACGCCGTAATGGAGAGTAGAGAGATAGAAAATGGCGATG

GAGCCAAGGAGTACTTGGTGAAATTTCCCGATGAAGATGAACCTGTGTGGGTCCAC

GAGAAGTACATGTCGGAAGAGGTCGTATCCGATTACCAAGATAACCTGGAGTACGC

GAAAGCTGAGAAGATTCTCGATGTCCGAAATAAGGGAGACTCTCGTGCGTATTTGGT

GAGATGGATGGATGGATCAGAGGACACCTGGGAGCCAGAGGAACATGTCTCCCAAG

ATCTCATCTACATGTTTGAGAACAACGGTGCTCTGCCTCCAGGTGTCAAAATCTAA

SEQ ID NO: 2, *Picochlorum* sp., PRT, allele A T4075215
sequence_region_id = 918410 length = 372, allele A
polypeptide encoded by SEQ ID NO: 1.
MEIINRNFIIAIGPHTRTAPRPGIRRTRQVLHDTGARRALFVFQTTPRACKA

QARLMIQAATEEIVEVKNLKGIRMKPRSAEDEEKKVRPMVEYLVEWKDGSPDTWEPVT

NLADNLLRDFESKWWNAVKKGDEAVMSEMLDGGGAVLSRTLNEDRRSALHFAAALG

KADLVRRLIREGAEVDLGDKEGYTPLHMAAGYLHTSTIYALIEGNADPEQQDLQGRSPL

ELVESLRAALPPDNPATAARRIALEEVLKVLVDNLFEDVLPDAVMESREIENGDGAKEY

LVKFPDEDEPVWVHEKYMSEEVVSDYQDNLEYAKAEKILDVRNKGDSRAYLVRWMD

GSEDTWEPEEHVSQDLIYMFENNGALPPGVKI

SEQ ID NO: 3, DNA, *Picochlorum* sp., C4067888
sequence_region_id = 918394 start = 16503 stop = 15610
length = 894, allele B of cpSRP43
ATGAAACCGCGCAGCGCCGAGGACGAGGAGAAAAAGGTTCGTCCAAT

GGTGGAGTACTTGGTAGAGTGGAAGGATGGGTCGCCAGATACATGGGAGCCCGTCA

CAAACCTCGCGGACAATTTGCTGAGAGATTTCGAATCCAAATGGTGGAACGCTGTCA

AAAAGGGAGACGAAGCTGTGATGAGCGAGATGCTCGACGGCGGAGGCGCTGTTTTG

TCACGAACCCTGAATGAGGACAGACGCAGTGCCCTCCATTTTGCGGCTGCTCTTGGG

AAAGCTGACCTGGTGCGGCGTCTCATCAGAGAGGGGGCCGAGGTGGACCTGGGAGA

TAAAGAAGGGTACACTCCTCTGCACATGGCCGCAGGATATCTTCATACATCGACAAT

ATACGCTTTGATAGAAGGGAATGCAGATCCAGAGCAGCAGGATTTGCAGGGCAGGT

CTCCCTTGGAACTTGTCGAAAGCCTGAGAGCAGCTCTGCCCCCGGATAATCCAGCGA

CTGCGGCTCGTAGAATTGCTCTAGAAGAGGTACTGAAAGTATTGGTGGATAATTTGT

TCGAAGATGTGCTTCCAGACGCCGTAATGGAGAGTAGAGAGATAGAAAATGGCGAT

GGAGCCAAGGAGTACTTGGTGAAATTTCCCGACGAAGATGAACCTGTGTGGGTCCA

CGAGAAGTACATGTCGGAAGAGGTCGTAGCCGATTACCAAGATAACCTGGAGTACG

CGAAAGCTGAGAAGATTCTCGATGTCCGAAATAAGGGAGACTCTCGTGCGTATTTG

GTGAGATGGATGGATGGATCAGAGGACACCTGGGAGCCAGAGGAACATGTCTCCCG

AGATCTCATCTACATGTTTGAGAACAACGGTGCTCTGCCTCCAGGTGTCAAAATCTA

A

SEQ ID NO: 4, PRT, *Picochlorum* sp., T4067888
sequence region_id = 918394 length = 297, allele B
polypeptide encoded by SEQ ID NO: 3
MKPRSAEDEEKKVRPMVEYLVEWKDGSPDTWEPVTNLADNLLRDFESK

WWNAVKKGDEAVMSEMLDGGGAVLSRTLNEDRRSALHFAAALGKADLVRRLIREGA

-continued

EVDLGDKEGYTPLHMAAGYLHTSTIYALIEGNADPEQQDLQGRSPLELVESLRAALPPD

NPATAARRIALEEVLKVLVDNLFEDVLPDAVMESREIENGDGAKEYLVKFPDEDEPVW

VHEKYMSEEVVADYQDNLEYAKAEKILDVRNKGDSRAYLVRWMDGSEDTWEPEEHV

SRDLIYMFENNGALPPGVKI

SEQ ID NO: 5, DNA, *Picochlorum* sp., promoter from LHCP-PSII gene
TCCAACCATCCAAAGCCCAGACGAGATTCAACTCATGTACACACCACC

ATGTCTCAGACCTGGAGCAGTCGGCTGGTTCCCAGAGCAGGGTAAGATTTGGGAAA

AGTACGGTCTCCCGAAATTCCTTGGACCTGATCCTTCAAAGAAGCTGAACAAGCAAG

ATACCAAGAAAGACATGTAAATCAGACCATATCGAAATCAAGATTGATTGATGACC

CCGGGGACAAAAGGACCCGAAACCACATCAAGATAACCAAAGATTTTTTCCTATCG

GCGATATATCACAAGATATCCCATCAAAGGGTCGATTTGATGGGACCATAGTGTCAT

TCTTCGTGTCATCCAAGGCCATCCTTTTCGGGAATCAATGTCCACGAAAATCTATGCT

GATGATCAAGACAGGATCTGCCCAACCCCGGTACTTTTAATTCTCGATAATTTCATTT

CCAGTCAAATTTCGACGATCTATTCAAACAAATCAAG

SEQ ID NO: 6, DNA, *Picochlorum* sp., terminator from LHCP-PSII gene
GTGTATAGTTTCCTTGAATATCCTTCAGGGGATGCCACATGGTAATGTT

TCATTGTGATGTGGTTGCATGACAAACAGGTGTCATCATCTCTTGAAGCGTAAAAAA

ATGGATGCAGTTTGAGCACCCTTGTATATTTTTTTTCCCAAAAATATTTGTGTAACAA

AACGCATCCATAGCTGTGAGCTAGTAGTAGTTTTACAAATGAAAAGAATCATTCATT

ATGATACATGATTATTATTCCTCACAGTACACGCACTCATTATTGAAAATTCGTCGCT

TTATTCCGTATTTATACATCTAGAGTTCTGTTCACGACTAACTAGACTGCTCAGTTGA

GCGAGCTCGGAGATCCAGGGCTGCGTTGCATATGGATATCTGGTGTTTCGAATGAAT

TTGACGATATAATATCAAACAGTCCATCTGGATTATCCGCATGCACCCAGTGGACCG

CTGTTTCGTAACAAATGAACCCGATGCCCA

SEQ ID NO: 7, DNA, *Picochlorum* sp., LHCP-PSI (LHC-21), T3376703
ATGATTGCCGCTATCAAGACAACTTCTCCTTTCCAGAGGACTTTGGCCC

AGCCAAAGCAGCAGCGTGCTTCTCACGTGGTTGCTGCTGCTCGCGACTGCTGGTTGC

CTGGATCTGATTTCCCAAAACGTACGTCACACATCTGCTACTTGATTAAAAAAATTAG

AGGGGTTTGAGGGCGACAGAGGCACGCGTATCTGCAAAGAGGTTGCAGCTCGTTGC

CAAGTATAGGGTCAGACAAAGATATGGTGGTCTCATCCAATGGTGTATAGTAGACC

ATGTGCATCAATCTGATCGTATTTTCTATCTTCAATGCAGACTTGGAGTCCTGCAAGC

TTCCAGGAAACTATGGATTCGATCCATTGGGATTGGGTGCCAATGATGAGCGTTTGA

AGTGGTTTGCCGAGTCTGAGCGTGTCCACGCTCGCTGGGCCATGTTGGGTGTTGCTG

GAATTTTGGCTCAGGAAATCACCCATCCAGAGGTTTTCTGGTACACCTCCGGAGCTG

ATGTGGAACTGCCATTCAACTTGGCCGGATTGGCAGCATTTGAATTGTTTGTCATGC

ACTGGGTTGAGTCCAAGCGTGGATATGATGTCTTGAAGCCAGGATCACAGGATCAG

GACCCAGTCTTCTCTCAGTACAAGCTTGCACCACACGAGGTCGGATACCCAGGAAG

CGTATTCGCTCCATTCGTTCCAGGAAACTTGGAGGAGCTCAAGGTGAAGGAGATTAA

GAATGGACGCTTGGCCATGTTGGCATTTATAGGATTCACCATGGCTGCCCAGGTGAC

TGGACTTAACCCATTAGCTGCCCTTTCTGAGCATTTGTCTGATCCAATCAACACCACC

-continued

ATGTTCTCCAAGGCTGTTGTGATTCCAGGACAGGCTGTGGTCCCAACATGCAAGATT

CCAGACTCTGTGACTGTGCAGGGATTGACCATCCCAGCTGGATGCTTCTTGCAGGGA

CTCTGGCCATAA

SEQ ID NO: 8, DNA, *Picochlorum* sp., LHCP-PSI (LHC-11), T3379623
ATGCTGACTGCTGCTAGAATCAACGTTGGATTGGCTGCTGTACGTTTTA

ACATCGACTTTAATACATGTTTATGCGGGTATCAGGGTAAACGTCTGCGAGAAAGAC

TGGATAAAACGGCTTGGGCCGAGGAGGGTGGGGTGGGGGATACGCTCGATCCTGTG

GATTAGAGACCGGTCGAATGAAATGTTTGATGGGGCGAGCCACGCTCTTTTAATACC

AAGGTGATTATGTTCAACTCATCGATGCCTTTTTTGTATTTTGCAGCGCCCAGTTGCC

AACACCTCTTCCAGAAGAAACGTATCTGCCAAGGCTGAGAGCCGCCCAATCTGGTA

CCCAGGAAACGAGGCTGAGGTCCCAGAGTACCTTGATGGAACCCTTGCTGGAGATT

TCGGATTTGATCCTCTCGGATTGGGATCTTCTCCAGAGCAGCTCGCATGGAATGTCC

AGGCTGAATTGATCCATGGACGCCTTGCTATGACTGCTGTTGCCGGTATTTTGTACA

CCTCTGTCGCTCACTCTGCTGGAGCTGATGTGCCAGAGTGGTACGAGGCCGGAAAGG

TCTACATGGACAAGAACCCAGAGGTTTCCTTCGGAGCTCTTGTGTGGACCACCATTG

CTCTCTCTGGATGGGTTGAGTTCAAGCGTCTTCAGGACATCAGAAACCCAGGATCTC

AGGGAGATGGATCCTTCTTGGGAATCACCGATGACTTCAAGGGTGTGTCCAACGGAT

ACCCAGGAGGAAAGTACTTTGATCCAATGGGACTCTCCCGTGGAGACGAAGCTAAA

TACGCCGAATACAAGGAGAAGGAGGTTAAGAACGGACGCCTTGCCATGGTTGCTTT

CCTCGGATTCGCTGCCCAGTATGCCGCCACAGGAAAGGGACCAATTGACAACTTGG

CTGCCCACTTGGCTGACCCAGCCCACGCCAACTTTGTCCACAACGGTATCTCCGTGC

CATTTATTTCCAACTAA

SEQ ID NO: 9, DNA, *Picochlorum* sp., LHCP-PSI T3377421
ATGCAGATTTCTCGTCCAGCTGGACGCCCAGCTCGCGGTCGCGTTGTC

GCCGCTGCAGCTGACCGTCCTCTTTGGGCCCCTGGGGTGGAGCCACCCACCTATCTT

GATGGGTCCCTCGCAGGCGATCGCGGTTTCGATCCAATCGGTCTTGGAGCTGACCCA

AAGGCCTTGAACTGGTATAGGGCTGCCGAGCTGGTCCACGCAAGATGGGCCATGCT

GGGAGTTGCAGGAATCTTGGCCCAGGAGATTGTGCACCCAGAGCAGTGGTGGTACA

CTTCTGGTCTCCCAGAAAACCTCCCAGCCATCGAAGTGGGGGGTAAGATGAACCTC

GGAGGACTGTTGGCCTGGGAATTCCTCCTCATGCATTGGGTTGAGGTTCGCCGCTGG

CAAGACATCCGCAAGCATGGATCGGTGAACACAGATCCTATTTTCAAGAATAACTCC

GTTCCAAACCCAGAACCAGGATATCCAGGAGGCGTGTTTGATCCCCTTGGATTTGGA

AAGGGAGACATGAAGACAATGCAGACGAGAGAGATCAAGAATGGGCGCTTGGCCA

TGATTGCTTTTGCTGGATTCACTCTCCAGGCCCAGGCCACCGGAAAGGGCCCAATTG

AGAACTTGCAAGATCACCTCGCAAATCCATTTGGAAATAATATCGGATCCAACATTG

GTGTTTGCCACGTCCCAGCCAGCGTGGACGTCCAAGGGTTGCAAATTCCTCTCACTT

GCTTGTGGCCAGGTCAGCTTCAGTAG

SEQ ID NO: 10, DNA, *Picochlorum* sp., LHCP-PSI, T3382021
ATGCAATCAACAGCTTCAATTAGCCGTACATCGGCCTTCGTTGGTCGC

TCTAGGGCTCAGGTGCGTGTGATGAACATGGATTGCGTCGATTGCTTGGACAAGAGT

CTTGCACTCTCTCAACAAGCGAAAAGACGACTCATATGGTTTGATTATTAAAAGAAT

AAAATACTCATAGGATCACGTGGATACCATGTGCAGGCCAGACGCTCTGCAGTGAC

-continued

TGTGTATGCTGCTGCTCGCCCTCTGTGGCAACCAGGAAGCACACCACCAGCCCATCT

CGATGGATCTCTTCCAGGAGACTTTGGATTCGATCCTTTGAACCTTGGAGCAAACAA

GGCTGCTCTGGACTGGTACCGTAATGCCGAGCTTCAGAACGGACGCTGGGCCATGG

CTGGTGTTGCTGGCATCTTGATTCCAAACATCCTTACCAAGGCTGGCGTGTTGGATG

TTCCAGACTGGTTTGTGGCTGGAAAGATTGCCCAGGAGAACTCTGCAATTCCATTCT

CTTCTCTGCTCATGGTTCAGCTCTTCCTTCACAACTTTGTTGAGATCAAGCGTTGGGA

GGACATGAAGAACCCAGGAAGCCAGGCAGAGCCAGGATCATTCCTCGGATTCGAGT

CTGCTTTCAAGGGAACTGGAGTTTCTGGATATCCAGGAGGTCCATTCGATCCTCTCG

GCCTTGCATCTGGATCCAAAGAGAGCGTTGATGACCTCAAACTGAAGGAGATTAAG

AATGGTCGCCTTGCCATGGTGGCCTTCCTTGGATTCGTTGCACAGCAGGCTGCCACA

GGAAAGGGACCAGTCGACAACTTGTTGGATCATATCGCCTCTCCATGGGCAGTGAA

CTTTTGCACAAACGGAGTCTCCCTTCCAGTGAGCATTTTCTAA

SEQ ID NO: 11, DNA, *Picochlorum* sp., LHCP-PSI, T3380921
ATGGTACAGATTTTGTCAGTCCCCATGCCTCCAAGCAGTCACAATCTT

ACACGTAATATTCAGAAACGTACTACCTTTGCAGCAATTAAGCGCGATGCAGGTACG

ATGCTTATATCTGTTCCCAGAGAAGGGCGTTGTCGTGGTGACGAAAGATTGGCTGTG

GATGAAACATCCAGACAGGCAGTCGCAGTGCACGACCTTGTCCTTTCAGGTCCATAC

TCCCATCTTATTTCATGATTCAAAGCATATTTATTGCATGTATATGCTGGAAAGAGAC

GGCTGCTGACGAGAGTCTTGTTGTTTTTTGTGCAGACTGTCAGTGTGAAATCCACCTT

TGCTACCACCCGTGTGGCTGCAACCCGTGCTAGCAGAGCTAGCGTACGTGTGTATGC

TGCTGATAGAACTCTCTGGTTGCCAGGAGCCACCGCTCCAAAGCACCTCGACGGAA

AGATGGCTGGAGATTTCGGATTTGATCCATTGGGATTGGGAACTGACCCAGAGCGCC

TCAAGTGGTATGCCGAGGCCGAGAAGACCAACGGCCGCTGGGCAATGGCTGCCTGC

GCCGGAATCCTCTTCACTGAGGTGCTCGGAAAGCCAAAGTGGTTCGAGGCTGGTGCC

GAAGAGTACTGGATGCCAAACAATGCATTGCTCGCTGTGGAAGCTGTGATCATGGG

ATTCTTGGAGCTCAAGAGATATCAGGGATGGAAGGACTCTGGAGTGTCTGGATTCAT

CAATGCATTCCCATTCGATCCAGCTGGAATGAACTCCCCAGATATGGCTGTTAAGGA

AGTGAAGAATGGCCGTCTTGCCATGGTTGCCTTTGTAGGATTTGCAGTTGCTGCTCTT

GTGACTCGTCAGGGACCAATCGAGGCCCTCACCAGCCATTTGGCCAGTCCATTCGAG

AACAATATTATCGGAAGCATTGCCAATCTTCCAAATGTGATTGGAAAGTAG

SEQ ID NO: 12, DNA, *Picochlorum* sp., LHCP-PSI, T3380916
ATGATGGCCTCGACAACCACTGCCCGTCATCTCTTCGCTGCCAAGAAC

ACGACCACCCGTGCTCGTAGTTCTTCTCACGTGTGCGCTGCTGCTCGACCAACATGG

TATCCAGGTATGTGTTTAATAGGTAATTGCTACTCGCATGGCGACCCTCTGACTGAC

ACTCTGTGTCTCTCTGATCATGAGCAGGTGCTGCTGCCCCAAAGCATTTGGATGGAT

CCATGCCAGGAGACTACGGATTCGACCCACTCCGCTTGGGAACCAACACCGAGGTT

CTCCCATACTATAGAGAAGCCGAGTTGACCAACGGCCGATGGGCCATGGCCGCCGT

GGCAGGAATCCTCTTCACTGACTTGGTGGGTGCTGGAGATTGGTGGACTGCCGGAGC

CAAGGAGTATGCCTTGGACAACAAGACCCTCTTGGCCGTGGAGATTCCAGTCATGGC

TGTCCTCGAAGCCCTCCGTGTCAAGGGATGGGAGAGGACCGGAGAGTCTGGTGCCT

TTGGCATGCACCCATTCGACCCAATGGGCATGGCCTCTGATGAGAAGAGACTCAAG

GAAATTAAAAATGCCCGTCTTGCCATGGTTGCCTTTATCGGATTCTGCTCCCAGGCT

-continued

GCTGTCCAGGGAATGGGACCAATCGAATGCTTGAAGAAGCATTTGGAAGACCCAGG

CCATAACAATATCTTCACCTCCTCCGTGGGAGCTGAAGCCACCGTAGCTGTCATGGC

CCTGTCCATTGCCCCAGTGATTCTCGAGGCCAAAAAGGCCCTGGGCGATGACGATG

AGGAATTCCGCCCAATCCCATGGTAA

SEQ ID NO: 13, DNA, *Picochlorum* sp., LHCP-PSI, T3380741
ATGTTAGCAGAACAAACCCTGGTGTGGGATGCGAGTACCGTGGAAAA

AATTAAATTTAAACCAATCACCATGTTGTGCACGGCTGTATCATCGACAACAAAGAC

ATCTCTTCTTGGTCGCACTGCGGCAGTGTCTTCCAAGAGGACAAGCCGAGTGGTGGT

GGTGCGTGCAGAGGAGGGAACCACTGACCTTGCCAAGGCCTCTGAGCGTGTGAAAA

AGGCCGGAGGATTGTATGCAAACTTTGCTTCCGATCAGTCATTGTCTTACTTGAACG

GATCTCTCCCAGGAGACTACGGATTCGATCCTTTGGGATTGTCTGACCCAGAGGGAG

CTGGAGGTTTCATCACCCCAGAATGGTTGTCCTACTCTGAGGTCATCCATGGACGTT

GGGCCATGCTTGGGGCCGCTGGATGCATTGCACCAGAGGTTTTGTCTGCCATGGGAT

TGATTCCACAGACTGGAGATGAGGCTGTGTGGTTCCGTTCCGGAGTGATCCCACCAG

CTGGTTCCTATGATAAATACTGGGTTGATCCATACACCTTGTTCTTTGTCGAGGTTGT

ATTGATGCAGTTTGCCGAGCTTAAGAGATACCAGGACTTCCGTTACCCAGGATCTCA

GGGAAAGCAATACTTCTTGGGAATGGAGGCTGCATTCAATGGCAGTGGAAACCCAG

CATACCCAGGAGGTCAGTTCTTCAACATGTTCAACTTGGGAAAGACCGAGGCTGCCA

TGAATGAATTGAAATTGAAGGAAATTAAGAATGGAAGGCTTGCTATGTTGGCCATG

TTCGGATACGGAGCACAGGCAGTCATGACCCAAAAGGGTCCTTTTGCCAACTTGGTA

GACCATCTTGCTGATCCAGTTCACAACAACATGTTGGGAAACTTTGCCAACGCAATG

AAGCATTAA

SEQ ID NO: 14, DNA, *Picochlorum* sp., LHCP-PSI, T3382646
ATGCAATCAACAGCTTCAATTAGCCGTACATCGGCCTTCGTTGGTCGC

TCTAGGGCTCAGGCCAGACGCTCTGCAGTGACTGTGTATGCTGCTGCTCGCCCTCTG

TGGCAACCAGGAAGCACACCACCAGCCCATCTCGATGGATCTCTTCCAGGAGACTTT

GGATTCGATCCTTTGAACCTTGGGAGCAAACAAGGCTGCTCTGGACTGGTACCGTAAT

GCCGAGCTTCAGAACGGACGCTGGGCCATGGCTGGTGTTGCTGGCATCTTGATTCCA

AACATCCTCACCAAGGCTGGCGTGTTGGATGTTCCAGACTGGTTTGTGGCTGGAAAG

ATTGCCCAGGAGAACTCTGCAATTCCATTCTCTTCTCTGCTCATGGTTCAGCTCTTCC

TTCACAACTTTGTTGAGATCAAGCGTTGGGAGGACATGAAGAACCCAGGAAGCCAG

GCAGAGCCAGGATCATTCCTCGGATTCGAGTCTGCTTTCAAGGGAACTGGAGTTTCT

GGATATCCAGGAGGTCCATTCGATCCTCTCGGCCTTGCATCTGGATCCAAAGAGAGC

GTTGATGACCTCAAACTGAAGGAGATTAAGAATGGTCGCCTTGCCATGGTGGCCTTC

CTTGGATTCGTTGCACAGCAGGCTGCCACAGGAAAGGGACCAGTCGACAACTTGTT

GGATCATATCGCCTCTCCATGGGCAGTGAACTTTTGCACAAACGGAGTCTCCCTTCC

AGTGAGCATTTTCTAA

SEQ ID NO: 15, DNA, *Picochlorum* sp., LHCP-PSI, T3376704
ATGCTCCTCACTTTATTTTCATTTGTTTGTACCACTACTACTTCAGTAAT

CGATCGATCGATACACGTGACGATGATGCAGACCTTCAAGAGTACCAATGTGCTGA

GAAGCAGCTTGACTGCTCGTCCGGTACGTGTGCCTTTGATTATGGATTCTTTTCTGTG

TGATGGGGGTTATAATATGCCATATAATGCAGGTGTCTCGTGTTCAGAGGGTATCTG

-continued

TGGTGACACAGAGTGCTGCTGGGAACTGGTTCCCAGGGTCTGAAACCCCAGCCCAC

TTGTCTAGTAGCTCTCTTCCAGGAAACTTTGGATTCGATCCATTGAACTTGGGTAAG

GACCCAGAGAAGTTGAAGTGGTATGCTCAGGCTGAGCTTCAGCACGCTCGTTGGGC

CATGTTGGGTGTTGCAGGTGTGTTGGGAGCAGAGGCTACTGGACATGATTGGTTCAC

TGCTGGATCCCAGGAGTACTTTGCCGACTCCAAGACATTGTTCGCTATTCAAATGTTT

TTGATGGCATGGGTTGAGATTCGTCGTCTTCAGGACATGAGAAAGCCAGGAAGTGC

CAACCAGGACCCAATCTTTTCAAATAACAAGCTTCCAGATGGAAATGAGCCAGGAT

ATCCAGGAGGAATCTTTGATCCAGCTGGATTTGCCAAGGGTGATGTGAACACATTGA

AGCTCAAGGAGATCAAGAATGGTCGCTTGGCTATGGTTGCATTTTTAGGATTTATTG

CACAGCACTCTGCCACTGGCAAGGGTCCTTTGACCAACTTGGCAGACCATCTTGCTG

ATCCATGGAGCAACTTGGTCATTACAAATGGAGTTTCTGTTCCATTTGCCACCCATG

ATGGAATTACATCATTCTGGTAA

SEQ ID NO: 16, DNA, target sequence for gRNA for T3376703
GCAGCAGCGTGCTTCTCACG

SEQ ID NO: 17, DNA, target sequence for gRNA for T3379623
GGAGAAGATCCCAATCCGAG

SEQ ID NO: 18, DNA, target sequence for gRNA for C4075215,
allele A (SEQ ID 1)
GGAGCCCGTCACAAACCTCGCGG SEQ ID NO: 19, DNA, target sequence for gRNA for C4067888,
allele B (SEQ 3)
TCCATTTTGCGGCTGCTCTTGGG SEQ ID NO: 20, DNA, alternate target sequence for gRNA for
C4067888, allele B (SEQ 3)
ATGAGCGAGATGCTCGACGGCGG SEQ ID NO: 21, PRT, *Picochlorum* sp., LHCP-PSI (LHCP-21),
encoded by SEQ ID NO: 7
MIAAIKTTSPFQRTLAQPKQQRASHVVAAARDCWLPGSDFPKHLESCKLP

GNYGFDPLGLGANDERLKWFAESERVHARWAMLGVAGILAQEITHPEVFWYTSGADV

ELPFNLAGLAAFELFVMHWVESKRGYDVLKPGSQDQDPVFSQYKLAPHEVGYPGSVFA

PFVPGNLEELKVKEIKNGRLAMLAFIGFTMAAQVTGLNPLAALSEHLSDPINTTMFSKA

VVIPGQAVVPTCKIPDSVTVQGLTIPAGCFLQGLWP

SEQ ID NO: 22, PRT, *Picochlorum* sp., LHCP-PSI (LHCP-11),
encoded by SEQ ID NO: 8
MLTAARINVGLAARPVANTSSRRNVSAKAESRPIWYPGNEAEVPEYLDG

TLAGDFGFDPLGLGSSPEQLAWNVQAELIHGRLAMTAVAGILYTSVAHSAGADVPEWY

EAGKVYMDKNPEVSFGALVWTTIALSGWVEFKRLQDIRNPGSQGDGSFLGITDDFKGV

SNGYPGGKYFDPMGLSRGDEAKYAEYKEKEVKNGRLAMVAFLGFAAQYAATGKGPID

NLAAHLADPAHANFVHNGISVPFISN

SEQ ID NO: 23, PRT, *Picochlorum* sp., LHCP-PSI (LHCP-11),
encoded by SEQ ID NO: 9
MQISRPAGRPARGRVVAAAADRPLWAPGVEPPTYLDGSLAGDRGFDPIG

LGADPKALNWYRAAELVHARWAMLGVAGILAQEIVHPEQWWYTSGLPENLPAIEVGG

KMNLGGLLAWEFLLMHWVEVRRWQDIRKHGSVNTDPIFKNNSVPNPEPGYPGGVFDP

LGFGKGDMKTMQTREIKNGRLAMIAFAGFTLQAQATGKGPIENLQDHLANPFGNNIGS

NIGVCHVPASVDVQGLQIPLTCLWPGQLQ

SEQ ID NO: 24, PRT, *Picochlorum* sp., LHCP-PSI (LHCP-11),
encoded by SEQ ID NO: 10
MQSTASISRTSAFVGRSRAQNKILIGSRGYHVQARRSAVTVYAAARPLWQ

PGSTPPAHLDGSLPGDFGFDPLNLGANKAALDWYRNAELQNGRWAMAGVAGILIPNIL

TKAGVLDVPDWFVAGKIAQENSAIPFSSLLMVQLFLHNFVEIKRWEDMKNPGSQAEPGS

FLGFESAFKGTGVSGYPGGPFDPLGLASGSKESVDDLKLKEIKNGRLAMVAFLGFVAQQ

AATGKGPVDNLLDHIASPWAVNFCTNGVSLPVSIF

SEQ ID NO: 25, PRT, *Picochlorum* sp., LHCP-PSI (LHCP-11),
encoded by SEQ ID NO: 11
MVQILSVPMPPSSHNLTRNIQKRTTFAAIKRDAAYLLHVYAGKRRLLTRV

LLFFVQTVSVKSTFATTRVAATRASRASVRVYAADRTLWLPGATAPKHLDGKMAGDF

GFDPLGLGTDPERLKWYAEAEKTNGRWAMAACAGILFTEVLGKPKWFEAGAEEYWMP

NNALLAVEAVIMGFLELKRYQGWKDSGVSGFINAFPFDPAGMNSPDMAVKEVKNGRL

AMVAFVGFAVAALVTRQGPIEALTSHLASPFENNIIGSIANLPNVIGK

SEQ ID NO: 26, PRT, *Picochlorum* sp., LHCP-PSI (LHCP-11),
encoded by SEQ ID NO: 12
MMASTTTARHLFAAKNTTTRARSSSHVCAAARPTWYPGAAAPKHLDGS

MPGDYGFDPLRLGTNTEVLPYYREAELTNGRWAMAAVAGILFTDLVGAGDWWTAGA

KEYALDNKTLLAVEIPVMAVLEALRVKGWERTGESGAFGMHPFDPMGMASDEKRLKEI

KNARLAMVAFIGFCSQAAVQGMGPIECLKKHLEDPGHNNIFTSSVGAEATVAVMALSIA

PVILEAKKALGDDDEEFRPIPW

SEQ ID NO: 27, PRT, *Picochlorum* sp., LHCP-PSI (LHCP-11),
encoded by SEQ ID NO: 13
MLAEQTLVWDASTVEKIKFKPITMLCTAVSSTTKTSLLGRTAAVSSKRTS

RVVVVRAEEGTTDLAKASERVKKAGGLYANFASDQSLSYLNGSLPGDYGFDPLGLSDP

EGAGGFITPEWLSYSEVIHGRWAMLGAAGCIAPEVLSAMGLIPQTGDEAVWFRSGVIPP

AGSYDKYWVDPYTLFFVEVVLMQFAELKRYQDFRYPGSQGKQYFLGMEAAFNGSGNP

AYPGGQFFNMFNLGKTEAAMNELKLKEIKNGRLAMLAMFGYGAQAVMTQKGPFANL

VDHLADPVHNNMLGNFANAMKH

SEQ ID NO: 28, PRT, *Picochlorum* sp., LHCP-PSI (LHCP-11),
encoded by SEQ ID NO: 14
MQSTASISRTSAFVGRSRAQARRSAVTVYAAARPLWQPGSTPPAHLDGSL

PGDFGFDPLNLGANKAALDWYRNAELQNGRWAMAGVAGILIPNILTKAGVLDVPDWF

VAGKIAQENSAIPFSSLLMVQLFLHNFVEIKRWEDMKNPGSQAEPGSFLGFESAFKGTGV

SGYPGGPFDPLGLASGSKESVDDLKLKEIKNGRLAMVAFLGFVAQQAATGKGPVDNLL

DHIASPWAVNFCTNGVSLPVSIF

SEQ ID NO: 29, PRT, *Picochlorum* sp., LHCP-PSI (LHCP-11),
encoded by SEQ ID NO: 15
MLLTLFSFVCTTTTSVIDRSIHVTMMQTFKSTNVLRSSLTARPVSRVQRVS

VVTQSAAGNWFPGSETPAHLSSSSLPGNFGFDPLNLGKDPEKLKWYAQAELQHARWA

MLGVAGVLGAEATGHDWFTAGSQEYFADSKTLFAIQMFLMAWVEIRRLQDMRKPGSA

NQDPIFSNNKLPDGNEPGYPGGIFDPAGFAKGDVNTLKLKEIKNGRLAMVAFLGFIAQH

SATGKGPLTNLADHLADPWSNLVITNGVSVPFATHDGITSFW

Although the invention has been described with reference to the presently preferred embodiment, it should be understood that various modifications can be made without departing from the spirit of the invention. Accordingly, the invention is limited only by the following claims.

What is claimed is:

1. A mutant Trebouxiophyte algal organism comprising: a disruption in a first allele of a gene encoding a chloroplastic signal recognition particle 43 (cpSRP43) protein having at least 90% sequence identity to either SEQ ID NO: 2 or 4, and comprising a second, active allele of the gene encoding a chloroplastic signal recognition particle 43 (cpSRP43) protein having at least 90% sequence identity to the other of SEQ ID NO: 2 or 4, that does not comprise a disruption, and wherein the first allele and the second allele are not the same allele.

2. The mutant Trebouxiophyte algal organism of claim 1 wherein the organism has at least 5% greater biomass productivity than a corresponding control organism not having the disruption of the first allele of the gene encoding a chloroplastic SRP43 protein.

3. The mutant Trebouxiophyte algal organism of claim 2 wherein the first allele of the gene encodes a cpSRP43 protein having at least 90% sequence identity to SEQ ID NO: 2 and the second allele encodes a cpSRP43 protein having at least 90% sequence identity to SEQ ID NO: 4.

4. The mutant Trebouxiophyte algal organism of claim 1 wherein the organism is of the genus *Picochlorum*.

5. The mutant Trebouxiophyte algal organism of claim 1 wherein the organism has a PSII σ450 value of less than 300 A$^2$, and a PSII σ520 value of less than 100 A$^2$.

6. The mutant Trebouxiophyte algal organism of claim 1 wherein the organism has a PSI σ450 value of less than 500 A$^2$, and a PSI σ520 value of less than 150 A$^2$.

7. The mutant Trebouxiophyte algal organism of claim 1 wherein the organism has a biomass productivity at least 7% higher than a corresponding control organism.

8. The mutant Trebouxiophyte algal organism of claim 1 wherein the organism has a ratio of PSI/PSII antenna cross section of less than 1.5.

9. The mutant Trebouxiophyte algal organism of claim 1 wherein the organism has a Chl a:b ratio of greater than 6.0.

10. The mutant Trebouxiophyte algal organism of claim 2 wherein the organism has:
    a PSII σ450 value of less than 300 A$^2$ and a PSII σ520 value of less than 100 A$^2$, or
    a PSI σ450 value of less than 500 A$^2$, and a PSI σ520 value of less than 150 A$^2$, or
    a PSI/PSII value of less than 0.65 and a Chl a:b ratio of greater than 6.0.

11. The mutant Trebouxiophyte algal organism of claim 3 wherein the organism is diploid.

12. The mutant Trebouxiophyte algal organism of claim 3 wherein the organism is polyploid.

13. The mutant Trebouxiophyte algal organism of claim 2 further comprising a disruption of a gene encoding a light harvesting chlorophyll a/b binding protein of PSI comprising at least 90% sequence identity to any one of SEQ ID NOs: 7-12.

14. The mutant Trebouxiophyte algal organism of claim 1 comprising a disruption of a gene encoding a light harvesting chlorophyll a/b binding protein LHCP-11 of PSI, and/or a gene encoding a light harvesting complex LHCP-21 of PSI.

15. The mutant Trebouxiophyte algal organism of claim 1 comprising a disruption of a gene encoding a light harvesting chlorophyll a/b binding protein of PSI having a polypeptide sequence with at least 90% sequence identity to SEQ ID NO: 21, or a disruption of a gene encoding a light harvesting complex of PSI having a polypeptide sequence with at least 90% sequence identity to SEQ ID NO: 22.

16. The mutant Trebouxiophyte algal organism of claim 2 comprising a disruption of a gene encoding a light harvesting chlorophyll a/b binding protein of PSI having a sequence with at least 90% sequence identity to SEQ ID NO: 7, and a disruption of a gene encoding a light harvesting complex of PSI having a sequence with at least 90% sequence identity to SEQ ID NO: 8.

17. The mutant Trebouxiophyte algal organism of claim 16 having a lipid productivity at least 4% higher than a corresponding control algal organism.

18. The mutant Trebouxiophyte algal organism of claim 16 wherein the mutant Trebouxiophyte algal organism is a member of the genus *Pichochlorum*.

19. A biomass comprising the mutant Trebouxiophyte algal organism of claim 1.

20. A biomass comprising the mutant Trebouxiophyte algal organism of claim 11.

21. A method of producing a lipid composition comprising culturing the mutant Trebouxiophyte algal organism of claim 1 in a culture medium to produce a biomass composition containing lipids.

22. The method of claim 21 further comprising harvesting a lipid product from the biomass composition.

23. A method of attenuating a pigment composition in a mutant Trebouxiophyte algal organism comprising:
    cultivating the mutant Trebouxiophyte algal organism of claim 1 to thereby attenuate the pigment in the mutant Trebouxiophyte algal organism.

24. The method of claim 23 wherein the mutant Trebouxiophyte algal organism is a member of the genus *Picochlorum*.

25. The method of claim 23 wherein the disruption is generated by exposing the mutant Trebouxiophyte algal organism to uv light and/or gamma radiation.

26. The method of claim 23 wherein the mutant Trebouxiophyte algal organism further comprises a disruption of a gene encoding a light harvesting (binding) protein having a polypeptide sequence with at least 90% sequence identity to SEQ ID NO: 21 or SEQ ID NO: 22.

* * * * *

SEQUENCE LISTING

<160> NUMBER OF SEQ ID NOS: 29

<210> SEQ ID NO 1
<211> LENGTH: 1119
<212> TYPE: DNA
<213> ORGANISM: Picochlorum sp.

<400> SEQUENCE: 1

```
atggaaatca taaacagaaa tttcattatt gcgattggtc ctcataccag gaccgctcct         60
cgacctggaa tccgtaggac aaggcaggtg ctgcacgaca ctggtgcaag acgggccctg        120
tttgtcttcc agacgactcc ccgagcgtgc aaagcccaag ctaggttgat gatccaagct        180
gcgactgagg aaattgtcga ggtcaagaat ctgaaaggca ttcgaatgaa accgcgcagc        240
gccgaggacg aggagaaaaa ggttcgtcca atggtggagt acttggtaga gtggaaggat        300
gggtcgccag atacatggga gcccgtcaca aacctcgcgg acaatttgct gagagatttt        360
gaatccaaat ggtggaacgc tgtcaaaaag ggagacgaag ctgtgatgag cgagatgctc        420
gacggcggag cgctgtcttt gtcacgaacc ctgaatgagg acaggcgcag tgctctccat        480
tttgcggctg ctcttgggaa agctgacctg gtgcggcgtc tcatcagaga ggggggccgag        540 gtggacctgg agataaaga agggtacact cctctgcaca tggccgcagg atatcttcat        600
acatcgacaa tatacgcttt gatagaaggg aatgcagatc cagagcagca ggatttgcag        660
ggcaggtctc ccttggaact tgtcgaaagc ctgagagcag ctctgcccccc ggataatcca        720 gcgactgcgg ctcgtagaat tgctctagaa gaggtactga agtattggt ggataatttg        780 ttcgaagatg tgcttccaga cgccgtaatg gagagtagag agatagaaaa tggcgatgga        840
gccaaggagt acttggtgaa atttcccgat gaagatgaac ctgtgtgggt ccacgagaag        900
tacatgtcgg aagaggtcgt atccgattac caagataacc tggagtacgc gaaagctgag        960
aagattctcg atgtccgaaa taagggagac tctcgtgcgt atttggtgag atggatggat       1020
ggatcagagg acacctggga gccagaggaa catgtctccc aagatctcat ctacatgttt       1080
gagaacaacg gtgctctgcc tccaggtgtc aaaatctaa                              1119
```

<210> SEQ ID NO 2
<211> LENGTH: 372
<212> TYPE: PRT
<213> ORGANISM: Picochlorum sp.

<400> SEQUENCE: 2

```
Met Glu Ile Ile Asn Arg Asn Phe Ile Ile Ala Ile Gly Pro His Thr
1               5                   10                  15

Arg Thr Ala Pro Arg Pro Gly Ile Arg Arg Thr Arg Gln Val Leu His
            20                  25                  30

Asp Thr Gly Ala Arg Arg Ala Leu Phe Val Phe Gln Thr Thr Pro Arg
        35                  40                  45

Ala Cys Lys Ala Gln Ala Arg Leu Met Ile Gln Ala Ala Thr Glu Glu
    50                  55                  60

Ile Val Glu Val Lys Asn Leu Lys Gly Ile Arg Met Lys Pro Arg Ser
65                  70                  75                  80

Ala Glu Asp Glu Glu Lys Lys Val Arg Pro Met Val Glu Tyr Leu Val
                85                  90                  95

Glu Trp Lys Asp Gly Ser Pro Asp Thr Trp Glu Pro Val Thr Asn Leu
            100                 105                 110

Ala Asp Asn Leu Leu Arg Asp Phe Glu Ser Lys Trp Trp Asn Ala Val
            115                 120                 125
```

```
Lys Lys Gly Asp Glu Ala Val Met Ser Glu Met Leu Asp Gly Gly Gly
    130                 135                 140

Ala Val Leu Ser Arg Thr Leu Asn Glu Asp Arg Arg Ser Ala Leu His
145                 150                 155                 160

Phe Ala Ala Ala Leu Gly Lys Ala Asp Leu Val Arg Arg Leu Ile Arg
                165                 170                 175

Glu Gly Ala Glu Val Asp Leu Gly Asp Lys Glu Gly Tyr Thr Pro Leu
            180                 185                 190

His Met Ala Ala Gly Tyr Leu His Thr Ser Thr Ile Tyr Ala Leu Ile
        195                 200                 205

Glu Gly Asn Ala Asp Pro Glu Gln Gln Asp Leu Gln Gly Arg Ser Pro
    210                 215                 220

Leu Glu Leu Val Glu Ser Leu Arg Ala Ala Leu Pro Pro Asp Asn Pro
225                 230                 235                 240

Ala Thr Ala Ala Arg Arg Ile Ala Leu Glu Glu Val Leu Lys Val Leu
                245                 250                 255

Val Asp Asn Leu Phe Glu Asp Val Leu Pro Asp Ala Val Met Glu Ser
            260                 265                 270

Arg Glu Ile Glu Asn Gly Asp Gly Ala Lys Glu Tyr Leu Val Lys Phe
        275                 280                 285

Pro Asp Glu Asp Glu Pro Val Trp Val His Glu Lys Tyr Met Ser Glu
    290                 295                 300

Glu Val Val Ser Asp Tyr Gln Asp Asn Leu Glu Tyr Ala Lys Ala Glu
305                 310                 315                 320

Lys Ile Leu Asp Val Arg Asn Lys Gly Asp Ser Arg Ala Tyr Leu Val
                325                 330                 335

Arg Trp Met Asp Gly Ser Glu Asp Thr Trp Glu Pro Glu Glu His Val
            340                 345                 350

Ser Gln Asp Leu Ile Tyr Met Phe Glu Asn Asn Gly Ala Leu Pro Pro
        355                 360                 365

Gly Val Lys Ile
    370
```

<210> SEQ ID NO 3
<211> LENGTH: 894
<212> TYPE: DNA
<213> ORGANISM: Picochlorum sp.

<400> SEQUENCE: 3

```
atgaaaccgc gcagcgccga ggacgaggag aaaaaggttc gtccaatggt ggagtacttg      60
gtagagtgga aggatgggtc gccagataca tgggagcccg tcacaaacct cgcggacaat     120
ttgctgagag atttcgaatc caaatggtgg aacgctgtca aaaagggaga cgaagctgtg     180
atgagcgaga tgctcgacgg cggaggcgct gttttgtcac gaaccctgaa tgaggacaga     240
cgcagtgccc tccattttgc ggctgctctt gggaaagctg acctggtgcg cgtctcatc      300 agagagggggg ccgaggtgga cctgggagat aaagaagggt acactcctct gcacatggcc     360
gcaggatatc ttcatacatc gacaatatac gctttgatag aagggaatgc agatccagag     420
cagcaggatt tgcagggcag gtctcccttg aacttgtcg aaagcctgag agcagctctg     480
cccccggata tccagcgac tgcggctcgt agaattgctc tagaagaggt actgaaagta     540
ttggtggata atttgttcga agatgtgctt ccagacgccg taatggagag tagagagata     600
gaaaatggcg atggagccaa ggagtacttg gtgaaatttc ccgacgaaga tgaacctgtg     660
```

-continued tgggtccacg agaagtacat gtcggaagag gtcgtagccg attaccaaga taacctggag    720
tacgcgaaag ctgagaagat tctcgatgtc cgaaataagg gagactctcg tgcgtatttg    780
gtgagatgga tggatggatc agaggacacc tgggagccag aggaacatgt ctcccgagat    840
ctcatctaca tgtttgagaa caacggtgct ctgcctccag gtgtcaaaat ctaa          894

<210> SEQ ID NO 4
<211> LENGTH: 297
<212> TYPE: PRT
<213> ORGANISM: Picochlorum sp.

<400> SEQUENCE: 4

Met Lys Pro Arg Ser Ala Glu Asp Glu Glu Lys Lys Val Arg Pro Met
1               5                   10                  15

Val Glu Tyr Leu Val Glu Trp Lys Asp Gly Ser Pro Asp Thr Trp Glu
            20                  25                  30

Pro Val Thr Asn Leu Ala Asp Asn Leu Leu Arg Asp Phe Glu Ser Lys
        35                  40                  45

Trp Trp Asn Ala Val Lys Lys Gly Asp Glu Ala Val Met Ser Glu Met
    50                  55                  60

Leu Asp Gly Gly Gly Ala Val Leu Ser Arg Thr Leu Asn Glu Asp Arg
65                  70                  75                  80

Arg Ser Ala Leu His Phe Ala Ala Ala Leu Gly Lys Ala Asp Leu Val
                85                  90                  95

Arg Arg Leu Ile Arg Glu Gly Ala Glu Val Asp Leu Gly Asp Lys Glu
            100                 105                 110

Gly Tyr Thr Pro Leu His Met Ala Ala Gly Tyr Leu His Thr Ser Thr
            115                 120                 125

Ile Tyr Ala Leu Ile Glu Gly Asn Ala Asp Pro Glu Gln Gln Asp Leu
        130                 135                 140

Gln Gly Arg Ser Pro Leu Glu Leu Val Glu Ser Leu Arg Ala Ala Leu
145                 150                 155                 160

Pro Pro Asp Asn Pro Ala Thr Ala Ala Arg Arg Ile Ala Leu Glu Glu
                165                 170                 175

Val Leu Lys Val Leu Val Asp Asn Leu Phe Glu Asp Val Leu Pro Asp
            180                 185                 190

Ala Val Met Glu Ser Arg Glu Ile Glu Asn Gly Asp Gly Ala Lys Glu
            195                 200                 205

Tyr Leu Val Lys Phe Pro Asp Glu Asp Glu Pro Val Trp Val His Glu
    210                 215                 220

Lys Tyr Met Ser Glu Glu Val Val Ala Asp Tyr Gln Asp Asn Leu Glu
225                 230                 235                 240

Tyr Ala Lys Ala Glu Lys Ile Leu Asp Val Arg Asn Lys Gly Asp Ser
                245                 250                 255

Arg Ala Tyr Leu Val Arg Trp Met Asp Gly Ser Glu Asp Thr Trp Glu
            260                 265                 270

Pro Glu Glu His Val Ser Arg Asp Leu Ile Tyr Met Phe Glu Asn Asn
            275                 280                 285

Gly Ala Leu Pro Pro Gly Val Lys Ile
    290                 295

<210> SEQ ID NO 5
<211> LENGTH: 483
<212> TYPE: DNA
<213> ORGANISM: Picochlorum sp.

```
<400> SEQUENCE: 5
tccaaccatc caaagcccag acgagattca actcatgtac acaccaccat gtctcagacc      60
tggagcagtc ggctggttcc cagagcaggg taagatttgg gaaaagtacg gtctcccgaa     120
attccttgga cctgatcctt caaagaagct gaacaagcaa gataccaaga aagacatgta     180
aatcagacca tatcgaaatc aagattgatt gatgaccccg gggacaaaag gacccgaaac     240
cacatcaaga taaccaaaga tttttcctta tcggcgatat atcacaagat atcccatcaa     300
agggtcgatt tgatgggacc atagtgtcat tcttcgtgtc atccaaggcc atccttttcg     360
ggaatcaatg tccacgaaaa tctatgctga tgatcaagac aggatctgcc caaccccggt     420
acttttaatt ctcgataatt tcatttccag tcaaatttcg acgatctatt caaacaaatc     480
aag                                                                   483

<210> SEQ ID NO 6
<211> LENGTH: 481
<212> TYPE: DNA
<213> ORGANISM: Picochlorum sp.

<400> SEQUENCE: 6
gtgtatagtt tccttgaata tccttcaggg gatgccacat ggtaatgttt cattgtgatg      60
tggttgcatg acaaacaggt gtcatcatct cttgaagcgt aaaaaaatgg atgcagtttg     120
agcacccttg tatatttttt ttcccaaaaa tatttgtgta acaaaacgca tccatagctg     180
tgagctagta gtagttttac aaatgaaaag aatcattcat tatgatacat gattattatt     240
cctcacagta cacgcactca ttattgaaaa ttcgtcgctt tattccgtat ttatacatct     300
agagttctgt tcacgactaa ctagactgct cagttgagcg agctcggaga tccagggctg     360
cgttgcatat ggatatctgg tgtttcgaat gaatttgacg atataatatc aaacagtcca     420
tctggattat ccgcatgcac ccagtggacc gctgtttcgt aacaaatgaa cccgatgccc     480
a                                                                     481

<210> SEQ ID NO 7
<211> LENGTH: 971
<212> TYPE: DNA
<213> ORGANISM: Picochlorum sp.

<400> SEQUENCE: 7
atgattgccg ctatcaagac aacttctcct ttccagagga ctttggccca gccaaagcag      60
cagcgtgctt ctcacgtggt tgctgctgct cgcgactgct ggttgcctgg atctgatttc     120
ccaaaacgta cgtcacacat ctgctacttg attaaaaaat tagaggggtt tgagggcgac     180
agaggcacgc gtatctgcaa agaggttgca gctcgttgcc aagtataggg tcagacaaag     240
atatggtggt ctcatccaat ggtgtatagt agaccatgtg catcaatctg atcgtatttt     300
ctatcttcaa tgcagacttg gagtcctgca agcttccagg aaactatgga ttcgatccat     360
tgggattggg tgccaatgat gagcgtttga agtggtttgc cgagtctgag cgtgtccacg     420
ctcgctgggc catgttgggt gttgctggaa ttttggctca ggaaatcacc catccagagg     480
ttttctggta cacctccgga gctgatgtgg aactgccatt caacttggcc ggattggcag     540
catttgaatt gtttgtcatg cactgggttg agtccaagcg tggatatgat gtcttgaagc     600
caggatcaca ggatcaggac ccagtcttct ctcagtacaa gcttgcacca cacgaggtcg     660
gatacccagg aagcgtattc gctccattcg ttccaggaaa cttggaggag ctcaaggtga     720
aggagattaa gaatggacgc ttggccatgt tggcatttat aggattcacc atggctgccc     780
```

```
aggtgactgg acttaaccca ttagctgccc tttctgagca tttgtctgat ccaatcaaca      840
ccaccatgtt ctccaaggct gttgtgattc caggacaggc tgtggtccca acatgcaaga      900
ttccagactc tgtgactgtg cagggattga ccatcccagc tggatgcttc ttgcagggac      960
tctggccata a                                                            971

<210> SEQ ID NO 8
<211> LENGTH: 973
<212> TYPE: DNA
<213> ORGANISM: Picochlorum sp.

<400> SEQUENCE: 8
atgctgactg ctgctagaat caacgttgga ttggctgctg tacgttttaa catcgacttt       60
aatacatgtt tatgcgggta tcagggtaaa cgtctgcgag aaagactgga taaaacggct      120
tgggccgagg agggtggggt gggggatacg ctcgatcctg tggattagag accggtcgaa      180
tgaaatgttt gatggggcga gccacgctct tttaatacca aggtgattat gttcaactca      240
tcgatgcctt ttttgtattt tgcagcgccc agttgccaac acctcttcca gaagaaacgt      300
atctgccaag gctgagagcc gcccaatctg tacccaggaa acgaggctg aggtcccaga      360 gtaccttgat ggaacccttg ctggagattt cggatttgat cctctcggat gggatcttc      420 tccagagcag ctcgcatgga atgtccaggc tgaattgatc catggacgcc ttgctatgac      480
tgctgttgcc ggtattttgt acacctctgt cgctcactct gctggagctg atgtgccaga      540
gtggtacgag gccggaaagg tctacatgga caagaaccca gaggtttcct tcggagctct      600
tgtgtggacc accattgctc tctctggatg ggttgagttc aagcgtcttc aggacatcag      660
aaacccagga tctcagggag atggatcctt cttgggaatc accgatgact tcaagggtgt      720
gtccaacgga tacccaggag gaaagtactt tgatccaatg ggactctccc gtggagacga      780
agctaaatac gccgaataca aggagaagga ggttaagaac ggacgccttg ccatggttgc      840
tttcctcgga ttcgctgccc agtatgccgc cacaggaaag ggaccaattg acaacttggc      900
tgcccacttg gctgacccag cccacgccaa ctttgtccac aacggtatct ccgtgccatt      960
tatttccaac taa                                                          973

<210> SEQ ID NO 9
<211> LENGTH: 753
<212> TYPE: DNA
<213> ORGANISM: Picochlorum sp.

<400> SEQUENCE: 9
atgcagattt ctcgtccagc tggacgccca gctcgcggtc gcgttgtcgc cgctgcagct       60
gaccgtcctc tttgggcccc tggggtggag ccacccacct atcttgatgg gtccctcgca      120
ggcgatcgcg gtttcgatcc aatcggtctt ggagctgacc caaaggcctt gaactggtat      180
agggctgccg agctggtcca cgcaagatgg gccatgctgg gagttgcagg aatcttggcc      240
caggagattg tgcacccaga gcagtggtgg tacacttctg gtctcccaga aaacctccca      300
gccatcgaag tggggggtaa gatgaacctc ggaggactgt tggcctggga attcctcctc      360
atgcattggg ttgaggttcg ccgctggcaa gacatccgca agcatggatc ggtgaacaca      420
gatcctattt tcaagaataa ctccgttcca aacccagaac caggatatcc aggaggcgtg      480
tttgatcccc ttggatttgg aaagggagac atgaagacaa tgcagacgag agagatcaag      540
aatgggcgct ggccatgat tgctttttgct ggattcactc tccaggccca ggccaccgga      600
```

-continued

```
aagggcccaa ttgagaactt gcaagatcac ctcgcaaatc catttggaaa taatatcgga      660
tccaacattg gtgtttgcca cgtcccagcc agcgtggacg tccaaggggtt gcaaattcct     720 ctcacttgct tgtggccagg tcagcttcag tag                                  753

<210> SEQ ID NO 10
<211> LENGTH: 885
<212> TYPE: DNA
<213> ORGANISM: Picochlorum sp.

<400> SEQUENCE: 10
atgcaatcaa cagcttcaat tagccgtaca tcggccttcg ttggtcgctc tagggctcag       60
gtgcgtgtga tgaacatgga ttgcgtcgat tgcttggaca agagtcttgc actctctcaa      120
caagcgaaaa gacgactcat atggtttgat tattaaaaga ataaaatact cataggatca      180
cgtggatacc atgtgcaggc cagacgctct gcagtgactg tgtatgctgc tgctcgccct      240
ctgtggcaac caggaagcac accaccagcc catctcgatg gatctcttcc aggagacttt      300
ggattcgatc ctttgaacct tggagcaaac aaggctgctc tggactggta ccgtaatgcc      360
gagcttcaga acggacgctg ggccatggct ggtgttgctg gcatcttgat tccaaacatc      420
cttaccaagg ctggcgtgtt ggatgttcca gactggtttg tggctggaaa gattgcccag      480
gagaactctg caattccatt ctcttctctg ctcatggttc agctcttcct tcacaacttt      540
gttgagatca agcgttggga ggacatgaag aacccaggaa gccaggcaga gccaggatca      600
ttcctcggat tcgagtctgc tttcaaggga actggagttt ctggatatcc aggaggtcca      660
ttcgatcctc tcggccttgc atctggatcc aaagagagcg ttgatgacct caaactgaag      720
gagattaaga atggtcgcct tgccatggtg gccttccttg gattcgttgc acagcaggct      780
gccacaggaa agggaccagt cgacaacttg ttggatcata tcgcctctcc atgggcagtg      840
aacttttgca caaacggagt ctcccttcca gtgagcattt tctaa                     885

<210> SEQ ID NO 11
<211> LENGTH: 954
<212> TYPE: DNA
<213> ORGANISM: Picochlorum sp.

<400> SEQUENCE: 11
atggtacaga ttttgtcagt ccccatgcct ccaagcagtc acaatcttac acgtaatatt       60
cagaaacgta ctacctttgc agcaattaag cgcgatgcag gtacgatgct tatatctgtt      120
cccagagaag ggcgttgtcg tggtgacgaa agattggctg tggatgaaac atccagacag      180
gcagtcgcag tgcacgacct tgtcctttca ggtccatact cccatcttat ttcatgattc      240
aaagcatatt tattgcatgt atatgctgga aagagacggc tgctgacgag agtcttgttg      300
ttttttgtgc agactgtcag tgtgaaatcc acctttgcta ccacccgtgt ggctgcaacc      360
cgtgctagca gagctagcgt acgtgtgtat gctgctgata gaactctctg gttgccagga      420
gccaccgctc caaagcacct cgacggaaag atggctggag atttcggatt tgatccattg      480
ggattgggaa ctgacccaga gcgcctcaag tggtatgccg aggccgagaa gaccaacggc      540
cgctgggcaa tggctgcctg cgccggaatc ctcttcactg aggtgctcgg aaagccaaag      600
tggttcgagg ctggtgccga agagtactgg atgccaaaca atgcattgct cgctgtggaa      660
gctgtgatca tgggattctt ggagctcaag agatatcagg gatggaagga ctctggagtg      720
tctggattca tcaatgcatt cccattcgat ccagctggaa tgaactcccc agatatggct      780
gttaaggaag tgaagaatgg ccgtcttgcc atggttgcct ttgtaggatt tgcagttgct      840
```

-continued

```
gctcttgtga ctcgtcaggg accaatcgag gccctcacca gccatttggc cagtccattc      900
gagaacaata ttatcggaag cattgccaat cttccaaatg tgattggaaa gtag            954

<210> SEQ ID NO 12
<211> LENGTH: 809
<212> TYPE: DNA
<213> ORGANISM: Picochlorum sp.

<400> SEQUENCE: 12
atgatggcct cgacaaccac tgcccgtcat ctcttcgctg ccaagaacac gaccacccgt       60
gctcgtagtt cttctcacgt gtgcgctgct gctcgaccaa catggtatcc aggtatgtgt      120
ttaataggta attgctactc gcatggcgac cctctgactg acactctgtg tctctctgat      180
catgagcagg tgctgctgcc ccaaagcatt tggatggatc catgccagga gactacggat      240
tcgacccact ccgcttggga accaacaccg aggttctccc atactataga gaagccgagt      300
tgaccaacgg ccgatgggcc atggccgccg tggcaggaat cctcttcact gacttggtgg      360
gtgctggaga ttggtggact gccggagcca aggagtatgc cttggacaac aagaccctct      420
tggccgtgga gattccagtc atggctgtcc tcgaagccct ccgtgtcaag ggatgggaga      480
ggaccggaga gtctggtgcc tttggcatgc acccattcga cccaatgggc atggcctctg      540
atgagaagag actcaaggaa attaaaaatg cccgtcttgc catggttgcc tttatcggat      600
tctgctccca ggctgctgtc cagggaatgg gaccaatcga atgcttgaag aagcatttgg      660
aagacccagg cctaacaat atcttcacct cctccgtggg agctgaagcc accgtagctg      720
tcatggccct gtccattgcc ccagtgattc tcgaggccaa aaaggccctg ggcgatgacg      780
atgaggaatt ccgcccaatc ccatggtaa                                        809

<210> SEQ ID NO 13
<211> LENGTH: 909
<212> TYPE: DNA
<213> ORGANISM: Picochlorum sp.

<400> SEQUENCE: 13
atgttagcag aacaaaccct ggtgtgggat gcgagtaccg tggaaaaaat taaatttaaa       60
ccaatcacca tgttgtgcac ggctgtatca tcgacaacaa agacatctct tcttggtcgc      120
actgcggcag tgtcttccaa gaggacaagc cgagtggtgg tggtgcgtgc agaggaggga      180
accactgacc ttgccaaggc ctctgagcgt gtgaaaaagg ccggaggatt gtatgcaaac      240
tttgcttccg atcagtcatt gtcttacttg aacggatctc tcccaggaga ctacggattc      300
gatcctttgg gattgtctga cccagaggga gctggaggtt tcatcacccc agaatggttg      360
tcctactctg aggtcatcca tggacgttgg gccatgcttg gggccgctgg atgcattgca      420
ccagaggttt tgtctgccat gggattgatt ccacagactg agatgaggc tgtgtggttc       480 cgttccggag tgatcccacc agctggttcc tatgataaat actgggttga tccatacacc      540
ttgttctttg tcgaggttgt attgatgcag tttgccgagc ttaagagata ccaggacttc      600
cgttacccag atctcaggg aaagcaatac ttcttgggaa tggaggctgc attcaatggc       660
agtggaaacc cagcataccc aggaggtcag ttcttcaaca tgttcaactt gggaaagacc      720
gaggctgcca tgaatgaatt gaaattgaag gaaattaaga tggaaggct tgctatgttg       780 gccatgttcg atacggagc acaggcagtc atgacccaaa agggtccttt tgccaacttg       840
gtagaccatc ttgctgatcc agttcacaac aacatgttgg gaaactttgc caacgcaatg      900
```

-continued

```
aagcattaa                                                             909

<210> SEQ ID NO 14
<211> LENGTH: 747
<212> TYPE: DNA
<213> ORGANISM: Picochlorum sp.

<400> SEQUENCE: 14
atgcaatcaa cagcttcaat tagccgtaca tcggccttcg ttggtcgctc tagggctcag    60
gccagacgct ctgcagtgac tgtgtatgct gctgctcgcc ctctgtggca accaggaagc   120
acaccaccag cccatctcga tggatctctt ccaggagact ttggattcga tcctttgaac   180
cttggagcaa acaaggctgc tctggactgg taccgtaatg ccgagcttca gaacggacgc   240
tgggccatgg ctggtgttgc tggcatcttg attccaaaca tcctcaccaa ggctggcgtg   300
ttggatgttc cagactggtt tgtggctgga aagattgccc aggagaactc tgcaattcca   360
ttctcttctc tgctcatggt tcagctcttc cttcacaact ttgttgagat caagcgttgg   420
gaggacatga agaacccagg aagccaggca gagccaggat cattcctcgg attcgagtct   480
gctttcaagg gaactggagt ttctggatat ccaggaggtc cattcgatcc tctcggcctt   540
gcatctggat ccaaagagag cgttgatgac ctcaaactga aggagattaa gaatggtcgc   600
cttgccatgg tggccttcct tggattcgtt gcacagcagg ctgccacagg aaagggacca   660
gtcgacaact tgttggatca tatcgcctct ccatgggcag tgaacttttg cacaaacgga   720
gtctcccttc cagtgagcat tttctaa                                        747

<210> SEQ ID NO 15
<211> LENGTH: 868
<212> TYPE: DNA
<213> ORGANISM: Picochlorum sp.

<400> SEQUENCE: 15
atgctcctca ctttattttc atttgtttgt accactacta cttcagtaat cgatcgatcg    60
atacacgtga cgatgatgca gaccttcaag agtaccaatg tgctgagaag cagcttgact   120
gctcgtccgg tacgtgtgcc tttgattatg gattcttttc tgtgtgatgg gggttataat   180
atgccatata atgcaggtgt ctcgtgttca gagggtatct gtggtgacac agagtgctgc   240
tgggaactgg ttcccagggt ctgaaacccc agcccacttg tctagtagct ctcttccagg   300
aaactttgga ttcgatccat tgaacttggg taaggaccca gagaagttga agtggtatgc   360
tcaggctgag cttcagcacg ctcgttgggc catgttgggt gttgcaggtg tgttgggagc   420
agaggctact ggacatgatt ggttcactgc tggatcccag gagtactttg ccgactccaa   480
gacattgttc gctattcaaa tgttttttgat ggcatgggtt gagattcgtc gtcttcagga   540
catgagaaag ccaggaagtg ccaaccagga cccaatcttt tcaaataaca agcttccaga   600
tggaaatgag ccaggatatc caggaggaat ctttgatcca gctggatttg ccaagggtga   660
tgtgaacaca ttgaagctca aggagatcaa gaatggtcgc ttggctatgg ttgcattttt   720
aggatttatt gcacagcact ctgccactgg caagggtcct ttgaccaact ggcagacca    780 tcttgctgat ccatggagca acttggtcat tacaaatgga gtttctgttc catttgccac   840
ccatgatgga attacatcat tctggtaa                                       868

<210> SEQ ID NO 16
<211> LENGTH: 20
<212> TYPE: DNA
<213> ORGANISM: Picochlorum sp.
```

-continued

```
<400> SEQUENCE: 16
gcagcagcgt gcttctcacg                                                  20

<210> SEQ ID NO 17
<211> LENGTH: 20
<212> TYPE: DNA
<213> ORGANISM: Picochlorum sp.

<400> SEQUENCE: 17
ggagaagatc ccaatccgag                                                  20

<210> SEQ ID NO 18
<211> LENGTH: 23
<212> TYPE: DNA
<213> ORGANISM: Picochlorum sp.

<400> SEQUENCE: 18
ggagcccgtc acaaacctcg cgg                                              23

<210> SEQ ID NO 19
<211> LENGTH: 23
<212> TYPE: DNA
<213> ORGANISM: Picochlorum sp.

<400> SEQUENCE: 19
tccattttgc ggctgctctt ggg                                              23

<210> SEQ ID NO 20
<211> LENGTH: 23
<212> TYPE: DNA
<213> ORGANISM: Picochlorum sp.

<400> SEQUENCE: 20
atgagcgaga tgctcgacgg cgg                                              23

<210> SEQ ID NO 21
<211> LENGTH: 260
<212> TYPE: PRT
<213> ORGANISM: Picochlorum sp.

<400> SEQUENCE: 21

Met Ile Ala Ala Ile Lys Thr Thr Ser Pro Phe Gln Arg Thr Leu Ala
1               5                   10                  15

Gln Pro Lys Gln Gln Arg Ala Ser His Val Val Ala Ala Ala Arg Asp
            20                  25                  30

Cys Trp Leu Pro Gly Ser Asp Phe Pro Lys His Leu Glu Ser Cys Lys
        35                  40                  45

Leu Pro Gly Asn Tyr Gly Phe Asp Pro Leu Gly Leu Gly Ala Asn Asp
    50                  55                  60

Glu Arg Leu Lys Trp Phe Ala Glu Ser Glu Arg Val His Ala Arg Trp
65                  70                  75                  80

Ala Met Leu Gly Val Ala Gly Ile Leu Ala Gln Glu Ile Thr His Pro
                85                  90                  95

Glu Val Phe Trp Tyr Thr Ser Gly Ala Asp Val Glu Leu Pro Phe Asn
            100                 105                 110

Leu Ala Gly Leu Ala Ala Phe Glu Leu Phe Val Met His Trp Val Glu
        115                 120                 125

Ser Lys Arg Gly Tyr Asp Val Leu Lys Pro Gly Ser Gln Asp Gln Asp
    130                 135                 140
```

-continued

```
Pro Val Phe Ser Gln Tyr Lys Leu Ala Pro His Glu Val Gly Tyr Pro
145                 150                 155                 160

Gly Ser Val Phe Ala Pro Phe Val Pro Gly Asn Leu Glu Glu Leu Lys
                165                 170                 175

Val Lys Glu Ile Lys Asn Gly Arg Leu Ala Met Leu Ala Phe Ile Gly
            180                 185                 190

Phe Thr Met Ala Ala Gln Val Thr Gly Leu Asn Pro Leu Ala Ala Leu
        195                 200                 205

Ser Glu His Leu Ser Asp Pro Ile Asn Thr Thr Met Phe Ser Lys Ala
    210                 215                 220

Val Val Ile Pro Gly Gln Ala Val Val Pro Thr Cys Lys Ile Pro Asp
225                 230                 235                 240

Ser Val Thr Val Gln Gly Leu Thr Ile Pro Ala Gly Cys Phe Leu Gln
                245                 250                 255

Gly Leu Trp Pro
            260
```

```
<210> SEQ ID NO 22
<211> LENGTH: 248
<212> TYPE: PRT
<213> ORGANISM: Picochlorum sp.

<400> SEQUENCE: 22
```

```
Met Leu Thr Ala Ala Arg Ile Asn Val Gly Leu Ala Ala Arg Pro Val
1               5                   10                  15

Ala Asn Thr Ser Ser Arg Arg Asn Val Ser Ala Lys Ala Glu Ser Arg
            20                  25                  30

Pro Ile Trp Tyr Pro Gly Asn Glu Ala Glu Val Pro Glu Tyr Leu Asp
        35                  40                  45

Gly Thr Leu Ala Gly Asp Phe Gly Phe Asp Pro Leu Gly Leu Gly Ser
    50                  55                  60

Ser Pro Glu Gln Leu Ala Trp Asn Val Gln Ala Glu Leu Ile His Gly
65                  70                  75                  80

Arg Leu Ala Met Thr Ala Val Ala Gly Ile Leu Tyr Thr Ser Val Ala
                85                  90                  95

His Ser Ala Gly Ala Asp Val Pro Glu Trp Tyr Glu Ala Gly Lys Val
            100                 105                 110

Tyr Met Asp Lys Asn Pro Glu Val Ser Phe Gly Ala Leu Val Trp Thr
        115                 120                 125

Thr Ile Ala Leu Ser Gly Trp Val Glu Phe Lys Arg Leu Gln Asp Ile
    130                 135                 140

Arg Asn Pro Gly Ser Gln Gly Asp Gly Ser Phe Leu Gly Ile Thr Asp
145                 150                 155                 160

Asp Phe Lys Gly Val Ser Asn Gly Tyr Pro Gly Gly Lys Tyr Phe Asp
                165                 170                 175

Pro Met Gly Leu Ser Arg Gly Asp Glu Ala Lys Tyr Ala Glu Tyr Lys
            180                 185                 190

Glu Lys Glu Val Lys Asn Gly Arg Leu Ala Met Val Ala Phe Leu Gly
        195                 200                 205

Phe Ala Ala Gln Tyr Ala Ala Thr Gly Lys Gly Pro Ile Asp Asn Leu
    210                 215                 220

Ala Ala His Leu Ala Asp Pro Ala His Ala Asn Phe Val His Asn Gly
225                 230                 235                 240

Ile Ser Val Pro Phe Ile Ser Asn
```

-continued

245

<210> SEQ ID NO 23
<211> LENGTH: 250
<212> TYPE: PRT
<213> ORGANISM: Picochlorum sp.

<400> SEQUENCE: 23

Met Gln Ile Ser Arg Pro Ala Gly Arg Pro Ala Arg Gly Arg Val Val
1               5                   10                  15

Ala Ala Ala Ala Asp Arg Pro Leu Trp Ala Pro Gly Val Glu Pro Pro
            20                  25                  30

Thr Tyr Leu Asp Gly Ser Leu Ala Gly Asp Arg Gly Phe Asp Pro Ile
        35                  40                  45

Gly Leu Gly Ala Asp Pro Lys Ala Leu Asn Trp Tyr Arg Ala Ala Glu
    50                  55                  60

Leu Val His Ala Arg Trp Ala Met Leu Gly Val Ala Gly Ile Leu Ala
65                  70                  75                  80

Gln Glu Ile Val His Pro Glu Gln Trp Trp Tyr Thr Ser Gly Leu Pro
                85                  90                  95

Glu Asn Leu Pro Ala Ile Glu Val Gly Gly Lys Met Asn Leu Gly Gly
            100                 105                 110

Leu Leu Ala Trp Glu Phe Leu Leu Met His Trp Val Glu Val Arg Arg
        115                 120                 125

Trp Gln Asp Ile Arg Lys His Gly Ser Val Asn Thr Asp Pro Ile Phe
    130                 135                 140

Lys Asn Asn Ser Val Pro Asn Pro Glu Pro Gly Tyr Pro Gly Gly Val
145                 150                 155                 160

Phe Asp Pro Leu Gly Phe Gly Lys Gly Asp Met Lys Thr Met Gln Thr
                165                 170                 175

Arg Glu Ile Lys Asn Gly Arg Leu Ala Met Ile Ala Phe Ala Gly Phe
                180                 185                 190

Thr Leu Gln Ala Gln Ala Thr Gly Lys Gly Pro Ile Glu Asn Leu Gln
        195                 200                 205

Asp His Leu Ala Asn Pro Phe Gly Asn Asn Ile Gly Ser Asn Ile Gly
    210                 215                 220

Val Cys His Val Pro Ala Ser Val Asp Val Gln Gly Leu Gln Ile Pro
225                 230                 235                 240

Leu Thr Cys Leu Trp Pro Gly Gln Leu Gln
                245                 250

<210> SEQ ID NO 24
<211> LENGTH: 261
<212> TYPE: PRT
<213> ORGANISM: Picochlorum sp.

<400> SEQUENCE: 24

Met Gln Ser Thr Ala Ser Ile Ser Arg Thr Ser Ala Phe Val Gly Arg
1               5                   10                  15

Ser Arg Ala Gln Asn Lys Ile Leu Ile Gly Ser Arg Gly Tyr His Val
            20                  25                  30

Gln Ala Arg Arg Ser Ala Val Thr Val Tyr Ala Ala Ala Arg Pro Leu
        35                  40                  45

Trp Gln Pro Gly Ser Thr Pro Pro Ala His Leu Asp Gly Ser Leu Pro
    50                  55                  60

Gly Asp Phe Gly Phe Asp Pro Leu Asn Leu Gly Ala Asn Lys Ala Ala

-continued

```
65              70              75              80

Leu Asp Trp Tyr Arg Asn Ala Glu Leu Gln Asn Gly Arg Trp Ala Met
            85              90              95

Ala Gly Val Ala Gly Ile Leu Ile Pro Asn Ile Leu Thr Lys Ala Gly
            100             105             110

Val Leu Asp Val Pro Asp Trp Phe Val Ala Gly Lys Ile Ala Gln Glu
            115             120             125

Asn Ser Ala Ile Pro Phe Ser Ser Leu Leu Met Val Gln Leu Phe Leu
            130             135             140

His Asn Phe Val Glu Ile Lys Arg Trp Glu Asp Met Lys Asn Pro Gly
145             150             155             160

Ser Gln Ala Glu Pro Gly Ser Phe Leu Gly Phe Glu Ser Ala Phe Lys
                165             170             175

Gly Thr Gly Val Ser Gly Tyr Pro Gly Gly Pro Phe Asp Pro Leu Gly
                180             185             190

Leu Ala Ser Gly Ser Lys Glu Ser Val Asp Asp Leu Lys Leu Lys Glu
                195             200             205

Ile Lys Asn Gly Arg Leu Ala Met Val Ala Phe Leu Gly Phe Val Ala
            210             215             220

Gln Gln Ala Ala Thr Gly Lys Gly Pro Val Asp Asn Leu Leu Asp His
225             230             235             240

Ile Ala Ser Pro Trp Ala Val Asn Phe Cys Thr Asn Gly Val Ser Leu
                245             250             255

Pro Val Ser Ile Phe
            260

<210> SEQ ID NO 25
<211> LENGTH: 269
<212> TYPE: PRT
<213> ORGANISM: Picochlorum sp.

<400> SEQUENCE: 25

Met Val Gln Ile Leu Ser Val Pro Met Pro Pro Ser Ser His Asn Leu
1               5               10              15

Thr Arg Asn Ile Gln Lys Arg Thr Thr Phe Ala Ala Ile Lys Arg Asp
            20              25              30

Ala Ala Tyr Leu Leu His Val Tyr Ala Gly Lys Arg Arg Leu Leu Thr
            35              40              45

Arg Val Leu Leu Phe Phe Val Gln Thr Val Ser Val Lys Ser Thr Phe
        50              55              60

Ala Thr Thr Arg Val Ala Ala Thr Arg Ala Ser Arg Ala Ser Val Arg
65              70              75              80

Val Tyr Ala Ala Asp Arg Thr Leu Trp Leu Pro Gly Ala Thr Ala Pro
                85              90              95

Lys His Leu Asp Gly Lys Met Ala Gly Asp Phe Gly Phe Asp Pro Leu
                100             105             110

Gly Leu Gly Thr Asp Pro Glu Arg Leu Lys Trp Tyr Ala Glu Ala Glu
                115             120             125

Lys Thr Asn Gly Arg Trp Ala Met Ala Ala Cys Ala Gly Ile Leu Phe
            130             135             140

Thr Glu Val Leu Gly Lys Pro Lys Trp Phe Glu Ala Gly Ala Glu Glu
145             150             155             160

Tyr Trp Met Pro Asn Asn Ala Leu Leu Ala Val Glu Ala Val Ile Met
                165             170             175
```

```
Gly Phe Leu Glu Leu Lys Arg Tyr Gln Gly Trp Lys Asp Ser Gly Val
            180             185             190

Ser Gly Phe Ile Asn Ala Phe Pro Phe Asp Pro Ala Gly Met Asn Ser
        195             200             205

Pro Asp Met Ala Val Lys Glu Val Lys Asn Gly Arg Leu Ala Met Val
    210             215             220

Ala Phe Val Gly Phe Ala Val Ala Ala Leu Val Thr Arg Gln Gly Pro
225             230             235             240

Ile Glu Ala Leu Thr Ser His Leu Ala Ser Pro Phe Glu Asn Asn Ile
            245             250             255

Ile Gly Ser Ile Ala Asn Leu Pro Asn Val Ile Gly Lys
        260             265
```

```
<210> SEQ ID NO 26
<211> LENGTH: 243
<212> TYPE: PRT
<213> ORGANISM: Picochlorum sp.

<400> SEQUENCE: 26
```

```
Met Met Ala Ser Thr Thr Thr Ala Arg His Leu Phe Ala Ala Lys Asn
1               5               10              15

Thr Thr Thr Arg Ala Arg Ser Ser Ser His Val Cys Ala Ala Ala Arg
            20              25              30

Pro Thr Trp Tyr Pro Gly Ala Ala Ala Pro Lys His Leu Asp Gly Ser
        35              40              45

Met Pro Gly Asp Tyr Gly Phe Asp Pro Leu Arg Leu Gly Thr Asn Thr
    50              55              60

Glu Val Leu Pro Tyr Tyr Arg Glu Ala Glu Leu Thr Asn Gly Arg Trp
65              70              75              80

Ala Met Ala Ala Val Ala Gly Ile Leu Phe Thr Asp Leu Val Gly Ala
            85              90              95

Gly Asp Trp Trp Thr Ala Gly Ala Lys Glu Tyr Ala Leu Asp Asn Lys
        100             105             110

Thr Leu Leu Ala Val Glu Ile Pro Val Met Ala Val Leu Glu Ala Leu
        115             120             125

Arg Val Lys Gly Trp Glu Arg Thr Gly Glu Ser Gly Ala Phe Gly Met
        130             135             140

His Pro Phe Asp Pro Met Gly Met Ala Ser Asp Glu Lys Arg Leu Lys
145             150             155             160

Glu Ile Lys Asn Ala Arg Leu Ala Met Val Ala Phe Ile Gly Phe Cys
            165             170             175

Ser Gln Ala Ala Val Gln Gly Met Gly Pro Ile Glu Cys Leu Lys Lys
            180             185             190

His Leu Glu Asp Pro Gly His Asn Asn Ile Phe Thr Ser Ser Val Gly
            195             200             205

Ala Glu Ala Thr Val Ala Val Met Ala Leu Ser Ile Ala Pro Val Ile
    210             215             220

Leu Glu Ala Lys Lys Ala Leu Gly Asp Asp Asp Glu Glu Phe Arg Pro
225             230             235             240

Ile Pro Trp
```

```
<210> SEQ ID NO 27
<211> LENGTH: 302
<212> TYPE: PRT
<213> ORGANISM: Picochlorum sp.
```

<400> SEQUENCE: 27

Met Leu Ala Glu Gln Thr Leu Val Trp Asp Ala Ser Thr Val Glu Lys
1               5                   10                  15

Ile Lys Phe Lys Pro Ile Thr Met Leu Cys Thr Ala Val Ser Ser Thr
            20                  25                  30

Thr Lys Thr Ser Leu Leu Gly Arg Thr Ala Ala Val Ser Ser Lys Arg
        35                  40                  45

Thr Ser Arg Val Val Val Val Arg Ala Glu Glu Gly Thr Thr Asp Leu
    50                  55                  60

Ala Lys Ala Ser Glu Arg Val Lys Lys Ala Gly Gly Leu Tyr Ala Asn
65                  70                  75                  80

Phe Ala Ser Asp Gln Ser Leu Ser Tyr Leu Asn Gly Ser Leu Pro Gly
                85                  90                  95

Asp Tyr Gly Phe Asp Pro Leu Gly Leu Ser Asp Pro Glu Gly Ala Gly
            100                 105                 110

Gly Phe Ile Thr Pro Glu Trp Leu Ser Tyr Ser Glu Val Ile His Gly
        115                 120                 125

Arg Trp Ala Met Leu Gly Ala Ala Gly Cys Ile Ala Pro Glu Val Leu
    130                 135                 140

Ser Ala Met Gly Leu Ile Pro Gln Thr Gly Asp Glu Ala Val Trp Phe
145                 150                 155                 160

Arg Ser Gly Val Ile Pro Pro Ala Gly Ser Tyr Asp Lys Tyr Trp Val
                165                 170                 175

Asp Pro Tyr Thr Leu Phe Phe Val Glu Val Val Leu Met Gln Phe Ala
            180                 185                 190

Glu Leu Lys Arg Tyr Gln Asp Phe Arg Tyr Pro Gly Ser Gln Gly Lys
        195                 200                 205

Gln Tyr Phe Leu Gly Met Glu Ala Ala Phe Asn Gly Ser Gly Asn Pro
    210                 215                 220

Ala Tyr Pro Gly Gly Gln Phe Phe Asn Met Phe Asn Leu Gly Lys Thr
225                 230                 235                 240

Glu Ala Ala Met Asn Glu Leu Lys Leu Lys Glu Ile Lys Asn Gly Arg
                245                 250                 255

Leu Ala Met Leu Ala Met Phe Gly Tyr Gly Ala Gln Ala Val Met Thr
            260                 265                 270

Gln Lys Gly Pro Phe Ala Asn Leu Val Asp His Leu Ala Asp Pro Val
        275                 280                 285

His Asn Asn Met Leu Gly Asn Phe Ala Asn Ala Met Lys His
    290                 295                 300

<210> SEQ ID NO 28
<211> LENGTH: 248
<212> TYPE: PRT
<213> ORGANISM: Picochlorum sp.

<400> SEQUENCE: 28

Met Gln Ser Thr Ala Ser Ile Ser Arg Thr Ser Ala Phe Val Gly Arg
1               5                   10                  15

Ser Arg Ala Gln Ala Arg Arg Ser Ala Val Thr Val Tyr Ala Ala Ala
            20                  25                  30

Arg Pro Leu Trp Gln Pro Gly Ser Thr Pro Pro Ala His Leu Asp Gly
        35                  40                  45

Ser Leu Pro Gly Asp Phe Gly Phe Asp Pro Leu Asn Leu Gly Ala Asn
    50                  55                  60

Lys Ala Ala Leu Asp Trp Tyr Arg Asn Ala Glu Leu Gln Asn Gly Arg
65                  70                  75                  80

Trp Ala Met Ala Gly Val Ala Gly Ile Leu Ile Pro Asn Ile Leu Thr
                85                  90                  95

Lys Ala Gly Val Leu Asp Val Pro Asp Trp Phe Val Ala Gly Lys Ile
            100                 105                 110

Ala Gln Glu Asn Ser Ala Ile Pro Phe Ser Ser Leu Leu Met Val Gln
            115                 120                 125

Leu Phe Leu His Asn Phe Val Glu Ile Lys Arg Trp Glu Asp Met Lys
        130                 135                 140

Asn Pro Gly Ser Gln Ala Glu Pro Gly Ser Phe Leu Gly Phe Glu Ser
145                 150                 155                 160

Ala Phe Lys Gly Thr Gly Val Ser Gly Tyr Pro Gly Gly Pro Phe Asp
                165                 170                 175

Pro Leu Gly Leu Ala Ser Gly Ser Lys Glu Ser Val Asp Asp Leu Lys
            180                 185                 190

Leu Lys Glu Ile Lys Asn Gly Arg Leu Ala Met Val Ala Phe Leu Gly
            195                 200                 205

Phe Val Ala Gln Gln Ala Ala Thr Gly Lys Gly Pro Val Asp Asn Leu
        210                 215                 220

Leu Asp His Ile Ala Ser Pro Trp Ala Val Asn Phe Cys Thr Asn Gly
225                 230                 235                 240

Val Ser Leu Pro Val Ser Ile Phe
                245

<210> SEQ ID NO 29
<211> LENGTH: 266
<212> TYPE: PRT
<213> ORGANISM: Picochlorum sp.

<400> SEQUENCE: 29

Met Leu Leu Thr Leu Phe Ser Phe Val Cys Thr Thr Thr Thr Ser Val
1               5                   10                  15

Ile Asp Arg Ser Ile His Val Thr Met Met Gln Thr Phe Lys Ser Thr
            20                  25                  30

Asn Val Leu Arg Ser Ser Leu Thr Ala Arg Pro Val Ser Arg Val Gln
            35                  40                  45

Arg Val Ser Val Val Thr Gln Ser Ala Ala Gly Asn Trp Phe Pro Gly
        50                  55                  60

Ser Glu Thr Pro Ala His Leu Ser Ser Ser Ser Leu Pro Gly Asn Phe
65                  70                  75                  80

Gly Phe Asp Pro Leu Asn Leu Gly Lys Asp Pro Glu Lys Leu Lys Trp
                85                  90                  95

Tyr Ala Gln Ala Glu Leu Gln His Ala Arg Trp Ala Met Leu Gly Val
            100                 105                 110

Ala Gly Val Leu Gly Ala Glu Ala Thr Gly His Asp Trp Phe Thr Ala
            115                 120                 125

Gly Ser Gln Glu Tyr Phe Ala Asp Ser Lys Thr Leu Phe Ala Ile Gln
        130                 135                 140

Met Phe Leu Met Ala Trp Val Glu Ile Arg Arg Leu Gln Asp Met Arg
145                 150                 155                 160

Lys Pro Gly Ser Ala Asn Gln Asp Pro Ile Phe Ser Asn Asn Lys Leu
                165                 170                 175

Pro Asp Gly Asn Glu Pro Gly Tyr Pro Gly Gly Ile Phe Asp Pro Ala
            180                 185                 190

-continued

```
Gly Phe Ala Lys Gly Asp Val Asn Thr Leu Lys Leu Lys Glu Ile Lys
        195                 200                 205

Asn Gly Arg Leu Ala Met Val Ala Phe Leu Gly Phe Ile Ala Gln His
    210                 215                 220

Ser Ala Thr Gly Lys Gly Pro Leu Thr Asn Leu Ala Asp His Leu Ala
225                 230                 235                 240

Asp Pro Trp Ser Asn Leu Val Ile Thr Asn Gly Val Ser Val Pro Phe
            245                 250                 255

Ala Thr His Asp Gly Ile Thr Ser Phe Trp
            260                 265
```